(12) United States Patent
Pavlovskaia et al.

(10) Patent No.: US 10,912,571 B2
(45) Date of Patent: Feb. 9, 2021

(54) GENERATION OF A MATING SURFACE MODEL FOR PATIENT SPECIFIC CUTTING GUIDE BASED ON ANATOMICAL MODEL SEGMENTATION

(71) Applicant: Howmedica Osteonics Corporation, Mahwah, NJ (US)

(72) Inventors: Elena I. Pavlovskaia, San Francisco, CA (US); Boris E. Shpungin, Pleasanton, CA (US); Oleg Mishin, Foster City, CA (US); Olga Sominskaya, Lafayette, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 1205 days.

(21) Appl. No.: 14/776,660

(22) PCT Filed: Mar. 17, 2014

(86) PCT No.: PCT/US2014/030496
§ 371 (c)(1),
(2) Date: Sep. 14, 2015

(87) PCT Pub. No.: WO2014/145691
PCT Pub. Date: Sep. 18, 2014

(65) Prior Publication Data
US 2016/0022370 A1 Jan. 28, 2016

Related U.S. Application Data

(60) Provisional application No. 61/794,514, filed on Mar. 15, 2013.

(51) Int. Cl.
*A61B 17/15* (2006.01)
*A61B 34/10* (2016.01)
(Continued)

(52) U.S. Cl.
CPC .......... *A61B 17/154* (2013.01); *A61B 17/155* (2013.01); *A61B 34/10* (2016.02);
(Continued)

(58) Field of Classification Search
CPC ....... A61B 19/50; A61B 34/10; A61B 17/154; A61B 17/155; A61B 2034/105; A61B 2034/108; A61B 2017/568; A61F 2/38
(Continued)

(56) References Cited

U.S. PATENT DOCUMENTS

| 5,368,478 A | 11/1994 | Andreiko et al. |
| 5,568,384 A | 10/1996 | Robb et al. |

(Continued)

FOREIGN PATENT DOCUMENTS

| WO | WO 2003/107275 A2 | 12/2003 |
| WO | WO 2006/092600 A1 | 9/2006 |

(Continued)

OTHER PUBLICATIONS

International Search Report and Written Opinion, PCT/US2014/030496, dated Aug. 6, 2014.
(Continued)

*Primary Examiner* — Rehana Perveen
*Assistant Examiner* — Justin C Mikowski
(74) *Attorney, Agent, or Firm* — Polsinelli PC

(57) ABSTRACT

A smooth mating surface model defining a mating surface of a customized arthroplasty jig is generated. For example, sagittal slices of a volumetric image of a patient bone are segmented with segmentation splines. An anatomically accurate model of the patient bone is generated from the segmentation splines. The anatomically accurate model includes anatomically accurate segmentation splines. The anatomically accurate segmentation splines are transformed into mating surface contours. Any inadequate segments of
(Continued)

the mating surface contours are modified to obtain modified mating surface contours. A mating surface model of the patient bone is generated based on the mating surface contours and the modified mating surface contours. Three-dimensional cross-sections of the mating surface model are smoothed to generate the smooth mating surface model.

13 Claims, 29 Drawing Sheets

(51) Int. Cl.
    *A61B 17/56*     (2006.01)
    *A61F 2/38*     (2006.01)

(52) U.S. Cl.
    CPC ... *A61B 2017/568* (2013.01); *A61B 2034/105* (2016.02); *A61B 2034/108* (2016.02); *A61F 2/38* (2013.01)

(58) Field of Classification Search
    USPC .................................................. 703/1
    See application file for complete search history.

(56) References Cited

U.S. PATENT DOCUMENTS

| | | | |
|---|---|---|---|
| 5,587,912 | A | 12/1996 | Andersson et al. |
| 5,768,413 | A | 6/1998 | Levin et al. |
| 5,880,962 | A | 3/1999 | Andersson et al. |
| 5,970,182 | A | 10/1999 | Goris |
| 6,345,112 | B1 | 2/2002 | Summers et al. |
| 6,556,696 | B1 | 4/2003 | Summers et al. |
| 6,711,432 | B1 | 3/2004 | Krause et al. |
| 6,771,262 | B2 | 8/2004 | Krishnan |
| 6,813,373 | B1 | 11/2004 | Suri et al. |
| 7,024,027 | B1 | 4/2006 | Suri et al. |
| 7,149,564 | B2 | 12/2006 | Vining et al. |
| 7,184,814 | B2* | 2/2007 | Lang .................. A61B 5/055 324/307 |
| 7,239,908 | B1* | 7/2007 | Alexander ............ A61B 5/055 378/21 |
| 7,457,444 | B2 | 11/2008 | Geiger et al. |
| 7,468,075 | B2 | 12/2008 | Lang et al. |
| 7,584,080 | B2 | 9/2009 | Taylor et al. |
| 7,630,550 | B2 | 12/2009 | Maroy et al. |
| 7,653,229 | B2 | 1/2010 | Kaufhold et al. |
| 7,822,244 | B2 | 10/2010 | Blumhofer |
| 7,831,078 | B2 | 11/2010 | Unal et al. |
| 7,837,621 | B2 | 11/2010 | Krause et al. |
| 7,853,310 | B2 | 12/2010 | Vining et al. |
| 7,873,403 | B2 | 1/2011 | Lachner et al. |
| 7,894,647 | B2 | 2/2011 | Zhou et al. |
| 7,952,595 | B2 | 5/2011 | Schiwietz et al. |
| 8,050,473 | B2 | 11/2011 | Udupa et al. |
| 8,055,046 | B2 | 11/2011 | Feilkas et al. |
| 8,073,216 | B2 | 12/2011 | Dawant et al. |
| 8,098,909 | B2 | 1/2012 | Hibbard et al. |
| 8,131,038 | B2 | 3/2012 | Saddi et al. |
| 8,135,186 | B2 | 3/2012 | Bouman et al. |
| 8,140,144 | B2 | 3/2012 | Dale et al. |
| 8,160,325 | B2 | 4/2012 | Zug et al. |
| 8,160,326 | B2 | 4/2012 | Zug et al. |
| 8,160,345 | B2 | 4/2012 | Pavlovskaia et al. |
| 8,275,446 | B2 | 9/2012 | Vining et al. |
| 8,289,317 | B2 | 10/2012 | Harvill |
| 8,311,306 | B2 | 11/2012 | Pavlovskaia et al. |
| 8,355,553 | B2 | 1/2013 | Fidrich et al. |
| 8,379,957 | B2 | 2/2013 | Slabaugh et al. |
| 8,384,716 | B2 | 2/2013 | Young et al. |
| 8,463,007 | B2 | 6/2013 | Steinberg et al. |
| 8,483,469 | B2 | 7/2013 | Pavlovskaia et al. |
| 8,532,361 | B2 | 9/2013 | Pavlovskaia et al. |
| 8,577,107 | B2 | 11/2013 | Hibbard et al. |
| 8,698,795 | B2 | 4/2014 | Grewer et al. |
| 8,724,881 | B2 | 5/2014 | Zheng et al. |
| 8,731,258 | B2 | 5/2014 | Hibbard et al. |
| 8,777,875 | B2 | 7/2014 | Park |
| 8,898,043 | B2 | 11/2014 | Ashby et al. |
| 8,929,621 | B2 | 1/2015 | Lathuiliere et al. |
| 8,948,472 | B2 | 2/2015 | Wohlgemuth et al. |
| 9,082,159 | B2 | 7/2015 | Reisman |
| 9,119,559 | B2 | 9/2015 | Collins et al. |
| 9,208,263 | B2 | 12/2015 | Pavlovskaia et al. |
| 9,214,028 | B2 | 12/2015 | Feilkas et al. |
| 9,218,524 | B2 | 12/2015 | Wang et al. |
| 9,292,933 | B2 | 3/2016 | Madabhushi et al. |
| 9,349,074 | B2 | 5/2016 | Choi et al. |
| 9,495,752 | B2 | 11/2016 | Wu et al. |
| 9,646,229 | B2 | 5/2017 | Sofka et al. |
| 9,675,461 | B2 | 6/2017 | Mahfouz |
| 9,687,259 | B2 | 6/2017 | Pavlovskaia et al. |
| 10,159,513 | B2 | 12/2018 | Pavlovskaia et al. |
| 2006/0094951 | A1* | 5/2006 | Dean .................. A61F 2/30942 600/407 |
| 2006/0111628 | A1 | 5/2006 | Tsai et al. |
| 2007/0015995 | A1* | 1/2007 | Lang .................. A61B 5/055 600/407 |
| 2007/0198022 | A1 | 8/2007 | Lang et al. |
| 2007/0276224 | A1* | 11/2007 | Lang .................. A61B 5/055 600/410 |
| 2009/0222015 | A1* | 9/2009 | Park .................. A61B 17/175 606/89 |
| 2010/0023015 | A1* | 1/2010 | Park .................. A61B 17/15 606/87 |
| 2010/0076563 | A1* | 3/2010 | Otto .................. A61B 5/103 623/20.14 |
| 2011/0282473 | A1* | 11/2011 | Pavlovskaia ............ G06F 19/00 700/98 |
| 2012/0203233 | A1 | 8/2012 | Yoshida et al. |
| 2012/0265496 | A1* | 10/2012 | Mahfouz ................ A61B 17/14 703/1 |
| 2014/0244220 | A1* | 8/2014 | McKinnon ................ A61F 2/02 703/1 |
| 2016/0074048 | A1 | 3/2016 | Pavlovskaia et al. |
| 2019/0282302 | A1* | 9/2019 | Park ........................ A61B 17/58 |

FOREIGN PATENT DOCUMENTS

| WO | WO 2007/097853 A2 | 8/2007 |
| WO | WO 2009/019617 A2 | 2/2009 |
| WO | WO 2009/134672 A1 | 11/2009 |

OTHER PUBLICATIONS

Amendment Under 37 C.F.R. 1.312, U.S. Appl. No. 12/386,105, filed Oct. 1, 2012, 6 pages.
Amendment Under 37 C.F.R. 1.312, U.S. Appl. No. 13/374,960, filed May 7, 2013, 6 pages.
Non-Final Office Action, U.S. Appl. No. 13/731,697, dated Jan. 29, 2015.
Non-Final Office Action, U.S. Appl. No. 12/386,105, dated Feb. 9, 2012, 30 pages.
Non-Final Office Action, U.S. Appl. No. 13/374,960, dated Aug. 1, 2012, 6 pages.
Notice of Allowance, U.S. Appl. No. 13/066,568, dated Oct. 26, 2011, 28 pages.
Notice of Allowance, U.S. Appl. No. 12/386,105, dated Jul. 5, 2012, 11 pages.
Notice of Allowance, U.S. Appl. No. 13/374,960, dated Nov. 2, 2012, 24 pages.
Notice of Allowance, U.S. Appl. No. 13/374,960, dated May 6, 2013, 20 pages.
Notice of Allowance, U.S. Appl. No. 13/573,662, dated Mar. 19, 2013, 34 pages.
Notice of Allowance, U.S. Appl. No. 13/731,697, dated Jul. 29, 2015.
Preliminary Amendment, U.S. Appl. No. 13/731,697, dated May 10, 2013, 6 pages.

(56) References Cited

OTHER PUBLICATIONS

Response to Non-Final Office Action, U.S. Appl. No. 13/731,697, dated May 26, 2015.
Response to Non-Final Office Action, U.S. Appl. No. 12/386,105, dated Jun. 8, 2012, 13 pages.
Response to Restriction Requirement, U.S. Appl. No. 12/386,105, dated Dec. 21, 2011, 9 pages.
Response to Restriction, U.S. Appl. No. 13/573,662, dated Feb. 8, 2013, 8 pages.
Restriction Requirement, U.S. Appl. No. 13/573,662, dated Jan. 17, 2013, 6 pages.
Restriction Requirement, U.S. Appl. No. 12/386,105, dated Oct. 24, 2011, 7 pages.
Audette et al. "An algorithmic overview of surface registration techniques for medical imaging." Medical Image Analysis, vol. 4, No. 3, Sep. 1, 2000, pp. 201-217.
Hafez et al., "Computer-Assisted Total Knee Arthroplasty Using Patient-Specific Templating," *Clinical Orthopaedics and Related Research*, No. 0, pp. 1-9, 2006.
Ibáñez et al., The ITK Software Guide, Second Edition, Updated for ITK version 2.4, Nov. 21, 2005, pp. 114, 396-411, and 426.
Seim H et al. "Segmentation of Bony structures with Ligament Attachment Sites." *Springer*, Apr. 6, 2008, pp. 207-211.
Xie et al. "Segmentation by surface-to-image registration." proceedings of SPIE, vol. 6144, Mar. 2, 2006, pp. 614405-1-614405-7.
EP Examination Report, EP09739422.5, dated Mar. 7, 2017.
EP Search Report, EP17191709.9, dated Apr. 26, 2018.
Final Office Action, U.S. Appl. No. 15/581,974, dated May 15, 2018.
Notice of Allowance, U.S. Appl. No. 15/581,974, dated Aug. 16, 2018.
Response to Final Office Action, U.S. Appl. No. 15/581,974, dated Jul. 16, 2018.
Response to Non-Final Office Action, U.S. Appl. No. 15/581,974, dated Feb. 2, 2018.

\* cited by examiner

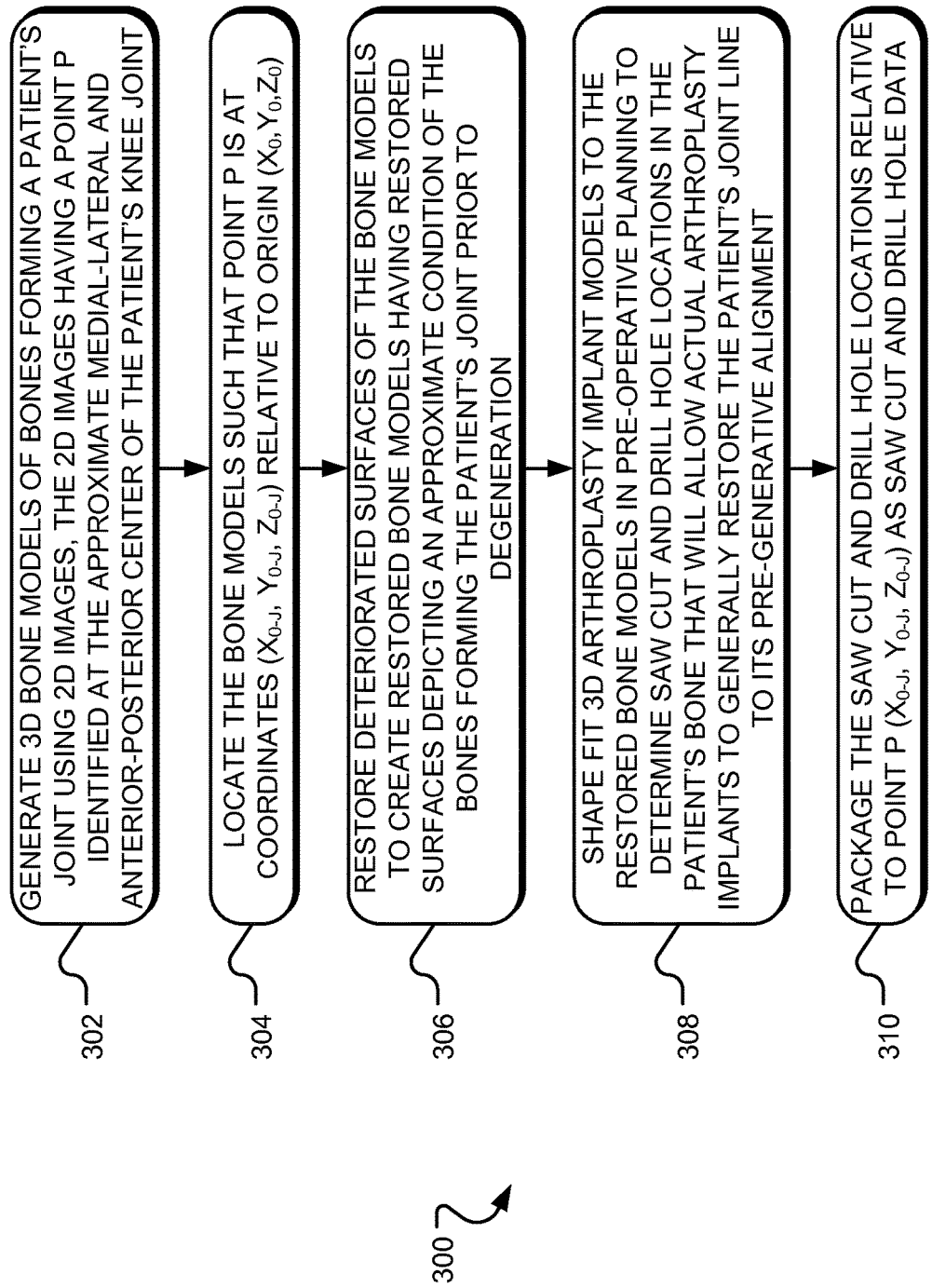

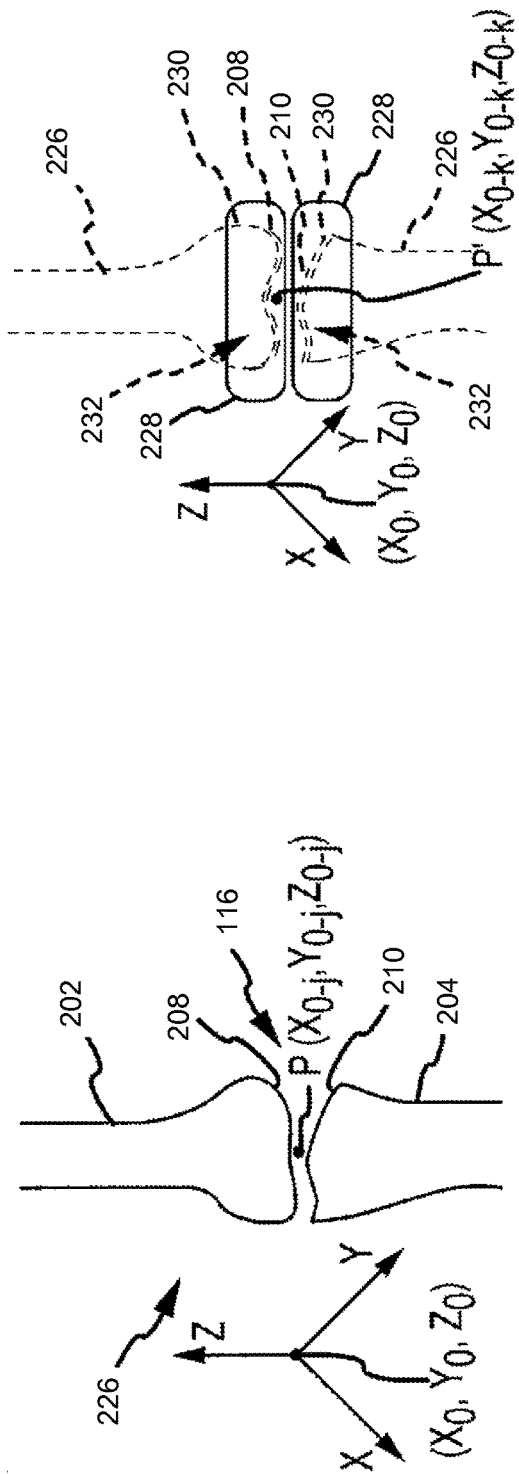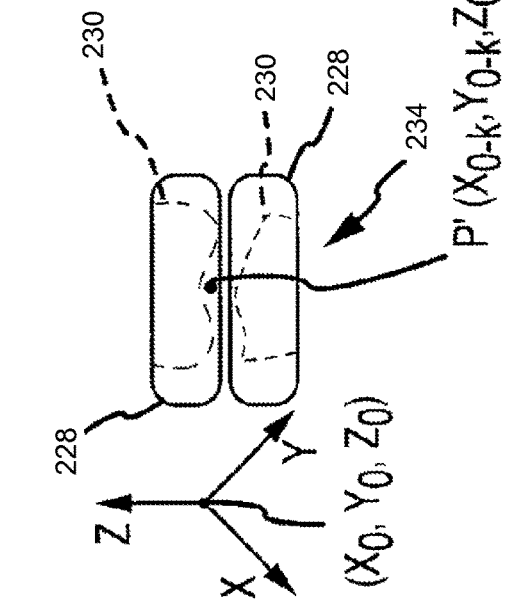

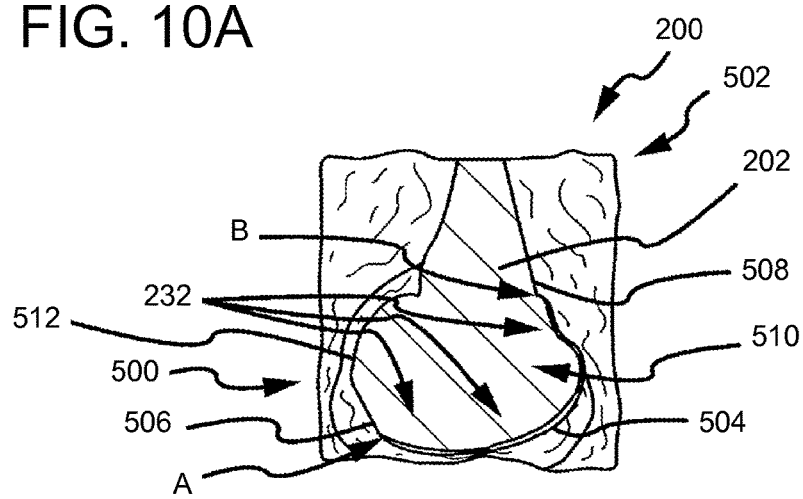
FIG. 10A
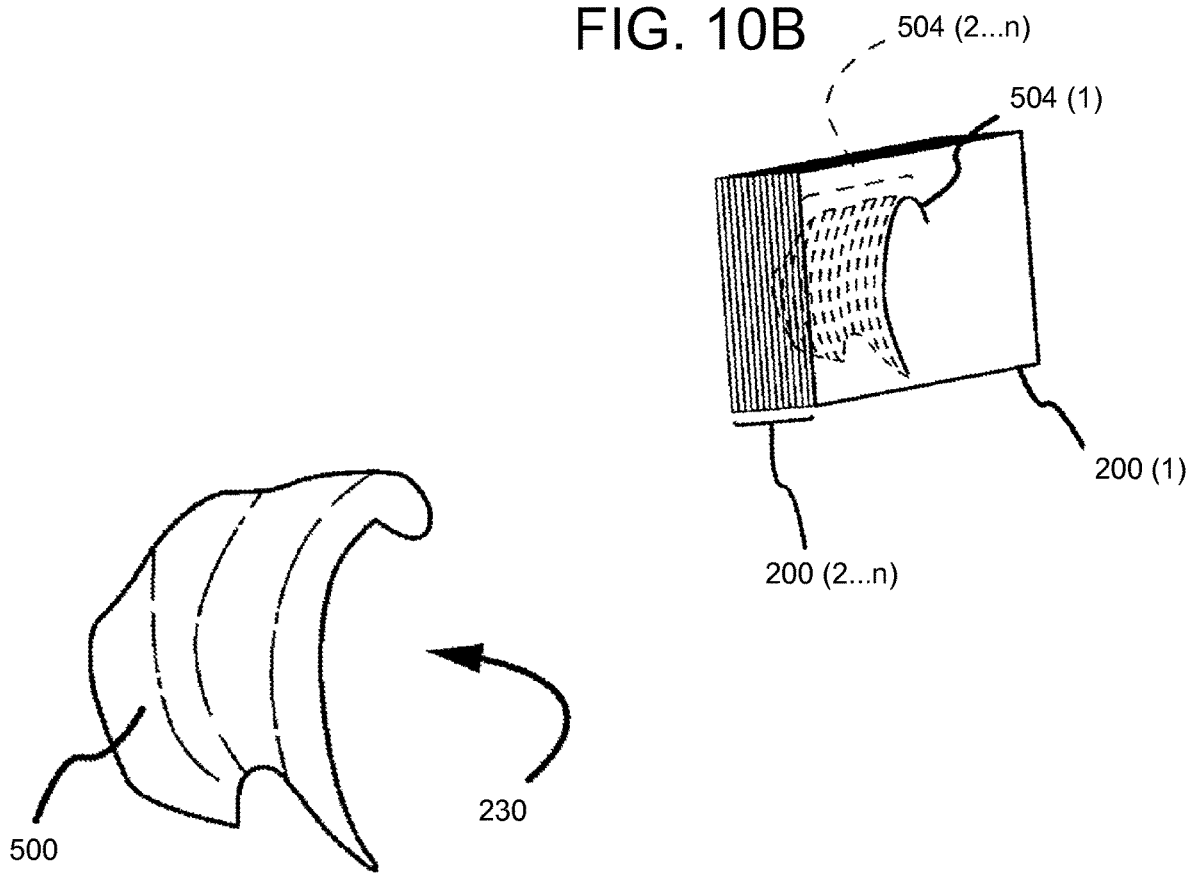
FIG. 10B
FIG. 10C

FIG. 11A
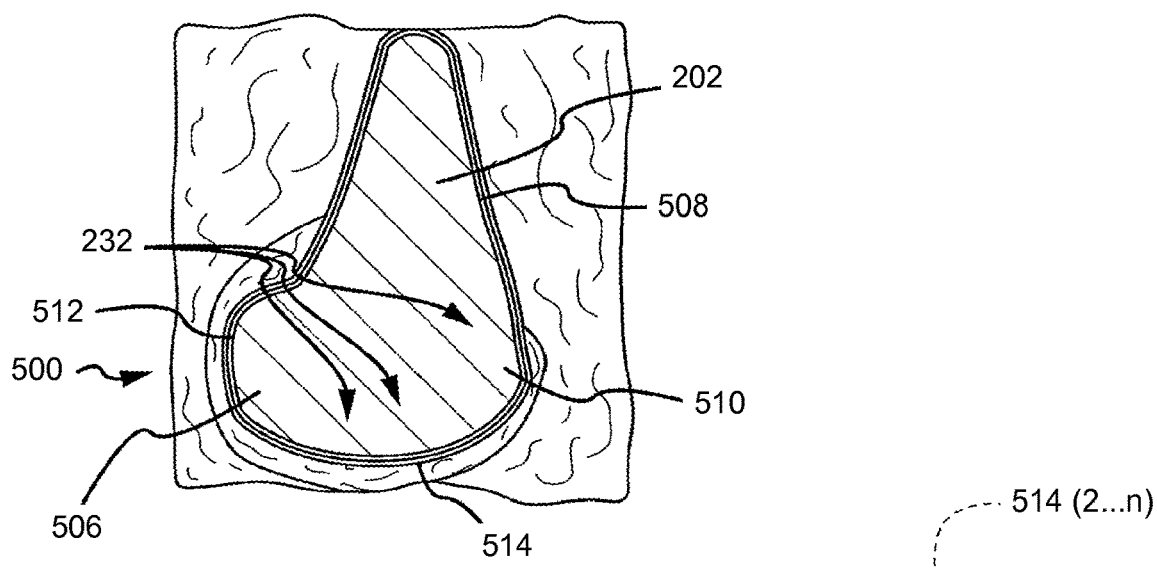
FIG. 11B
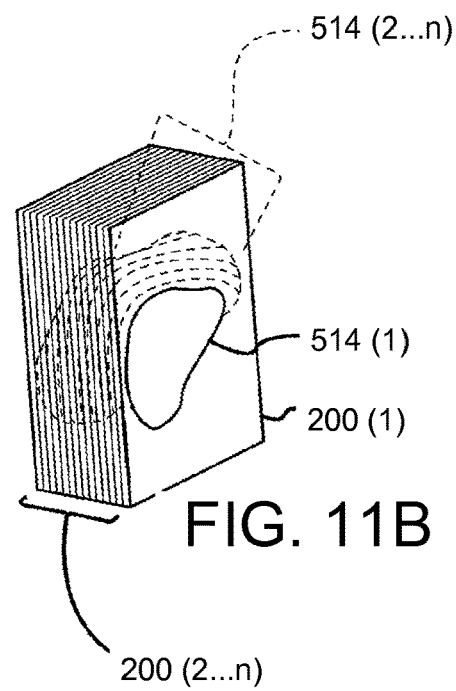
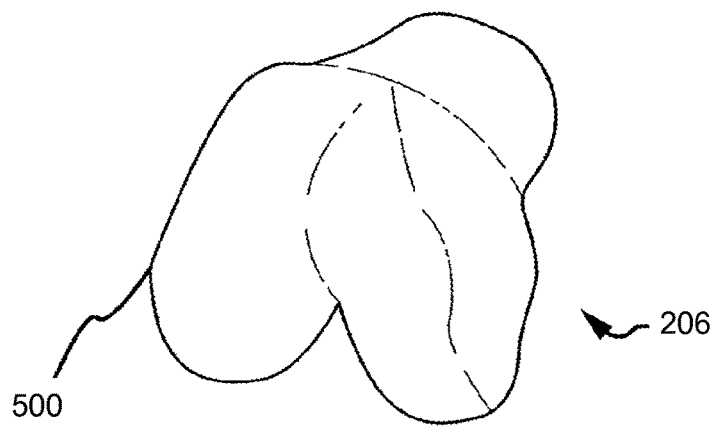
FIG. 11C

GENERATION OF A MATING SURFACE MODEL FOR PATIENT SPECIFIC CUTTING GUIDE BASED ON ANATOMICAL MODEL SEGMENTATION

CROSS-REFERENCE TO RELATED APPLICATIONS

The present application is a continuation-in-part of U.S. patent application Ser. No. 12/546,545, entitled "Arthroplasty System and Related Methods" and filed Aug. 24, 2009, which is a continuation-in-part of U.S. patent application Ser. No. 11/959,344, entitled "System and Method for Manufacturing Arthroplasty Jigs" and filed Dec. 18, 2007, and claims priority under 35 U.S.C. § 119 to U.S. Provisional Application No. 61/102,692, entitled "Arthroplasty System and Related Methods" and filed Oct. 3, 2008.

The present application is a continuation-in-part of U.S. patent application Ser. No. 12/505,056, entitled "System and Method for Manufacturing Arthroplasty Jigs having Improved Mating Accuracy" and filed Jul. 17, 2009, which claims priority under 35 U.S.C. § 119 to U.S. Provisional Application No. 61/083,053, entitled "System and Method for Manufacturing Arthroplasty Jigs having Improved Mating Accuracy" and filed Jul. 23, 2008.

The present application claims priority under 35 U.S.C. § 119 to U.S. Provisional Application No. 61/794,514, entitled "Generation of a Mating Surface Model for Patient Specific Cutting Guide based on Anatomical Model Segmentation" and filed Mar. 15, 2013.

Each of the aforementioned applications is hereby incorporated by reference in its entirety into the present application.

TECHNICAL FIELD

Aspects of the present disclosure generally relate to systems, apparatuses, and methods for designing and manufacturing customized medical cutting jigs. More specifically, one aspect of the present disclosure relates to patient specific mating cutting jigs for knee arthroplasty.

BACKGROUND

There are a number of abnormalities and conditions involving degradation of joints where the bones become damaged or worn. Generally, cartilage provides a cushioning effect to protect joint areas. However, repetitive strain on joints, traumatic events, and certain diseases (e.g., arthritis) can cause cartilage loss in the joint areas. Cartilage loss may expose and damage bone surfaces in the joint areas and can cause fluid to accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA") in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region and may help to restore the damaged region, thereby enhancing its functionality. Prior to implantation, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one to two millimeter translational misalignment or a one to two degree rotational misalignment may result in imbalanced ligaments, significantly affecting the outcome of the TKA procedure. For example, implant misalignment may result in intolerable post-surgery pain and/or prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on an operator to construct and orient a three-dimensional bone model. This often involves a human to "eyeball" bone models on a computer screen to determine configurations needed for the generation of the customized jigs. This is "eyeballing" or manual manipulation of the bone modes on the computer screen is inefficient and unnecessarily raises the time, manpower, and costs associated with producing the customized arthroplasty jigs. Furthermore, a less manual approach may improve the accuracy of the resulting jigs.

There is a need in the art for a system and method for reducing the resources expending in generating customized arthroplasty jigs, as well as a need for reducing the effects of operator error and for increasing the accuracy of such jigs. It is with these observations in mind, among others, that various aspects of the present disclosure were conceived and developed.

SUMMARY

Implementations described and claimed herein address the foregoing problems, among others, by providing systems and methods for generating a mating surface model for patient specific cutting guide based on anatomical model segmentation. In one implementation, sagittal slices of a volumetric image of a patient bone are segmented with segmentation splines. An anatomically accurate model of the patient bone is generated from the segmentation splines. The anatomically accurate model includes anatomically accurate segmentation splines. The anatomically accurate segmentation splines are transformed into mating surface contours. Any inadequate segments of the mating surface contours are modified to obtain modified mating surface contours. A mating surface model of the patient bone is generated based on the mating surface contours and the modified mating surface contours. Three-dimensional cross-sections of the mating surface model are smoothed to generate the smooth mating surface model.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 4 illustrates example operations for determining saw cut locations and drill hole locations in the patient's bones allowing arthroplasty joint implants to generally restore the patient's joint line to its pre-degenerative alignment.

FIGS. 5A-5C show three-dimensional arthritic models of the bones and cartilage forming the patient's joint generated using the two-dimensional images of FIGS. 2A and 2B.

FIG. 10A is an anterior-posterior image slice of a damaged lower or knee joint end of the patient's femur, wherein the image slice includes an open-loop contour line segment corresponding to the targeted region of the damaged lower end.

FIG. 10B is a plurality of image slices with their respective open-loop contour line segments, the open-loop contour line segments being accumulated to generate the three-dimensional model of the targeted region.

FIG. 10C is a three-dimensional model of the targeted region of the damaged lower end as generated using the open-loop contour line segments depicted in FIG. 10B.

FIG. 11A is an anterior-posterior image slice of the damaged lower or knee joint end of the patient's femur, wherein the image slice includes a closed-loop contour line corresponding to the femur lower end, including the targeted region.

FIG. 11B is a plurality of image slices with their respective closed-loop contour line segments, the closed-loop contour lines being accumulated to generate the three-dimensional model of the femur lower end, including the targeted region.

FIG. 11C is a three-dimensional model of the femur lower end, including the targeted region, generated using the closed-loop contour lines depicted in FIG. 10B.

DETAILED DESCRIPTION

Aspects of the present disclosure involve systems and methods for designing and manufacturing customized arthroplasty jigs. Generally, the systems and methods generate a smooth mating surface model, extending along at least one of a bone, cartilage, or osteophyte surface of a medical image of a patient joint or bone. The systems and methods further determine and apply various adjustments and overestimations to compensate for constraints in imaging, manufacturability, and surgical application. In one aspect, the mating surface model is generated from an anatomically accurate model of the bone created by drawing segmentation splines in sagittal slices of a volumetric image. General surface smoothing and image quality compensation rules and algorithms are applied to transform anatomically accurate segmentation splines into mating surface contours. Subsequently, the mating surface contours are further modified to accommodate manufacturing and surgical constraints and are further smoothed in all three-dimensional ("3D") cross-sections in a manner that does not impinge on actual underlying surfaces of the bone, cartilage, or osteophytes.

The systems and methods may be used to generate a mating surface model for a distal region of the femur of a patient to produce a patient specific cutting guide for total knee arthroplasty ("TKA"), to generate a mating surface model for a proximal region of the tibia of a patient to produce a patient specific cutting guide for total knee arthroplasty ("TKA"), or the like. While various implementations are described herein with respect to femur models, it will be appreciated by those skilled in the art that the systems and methods may be used to generate a mating surface model for any bone in any joint, including, without limitation, hip, shoulder, spine, cranial, elbow, wrist, ankle, and other joints.

Figure 1:
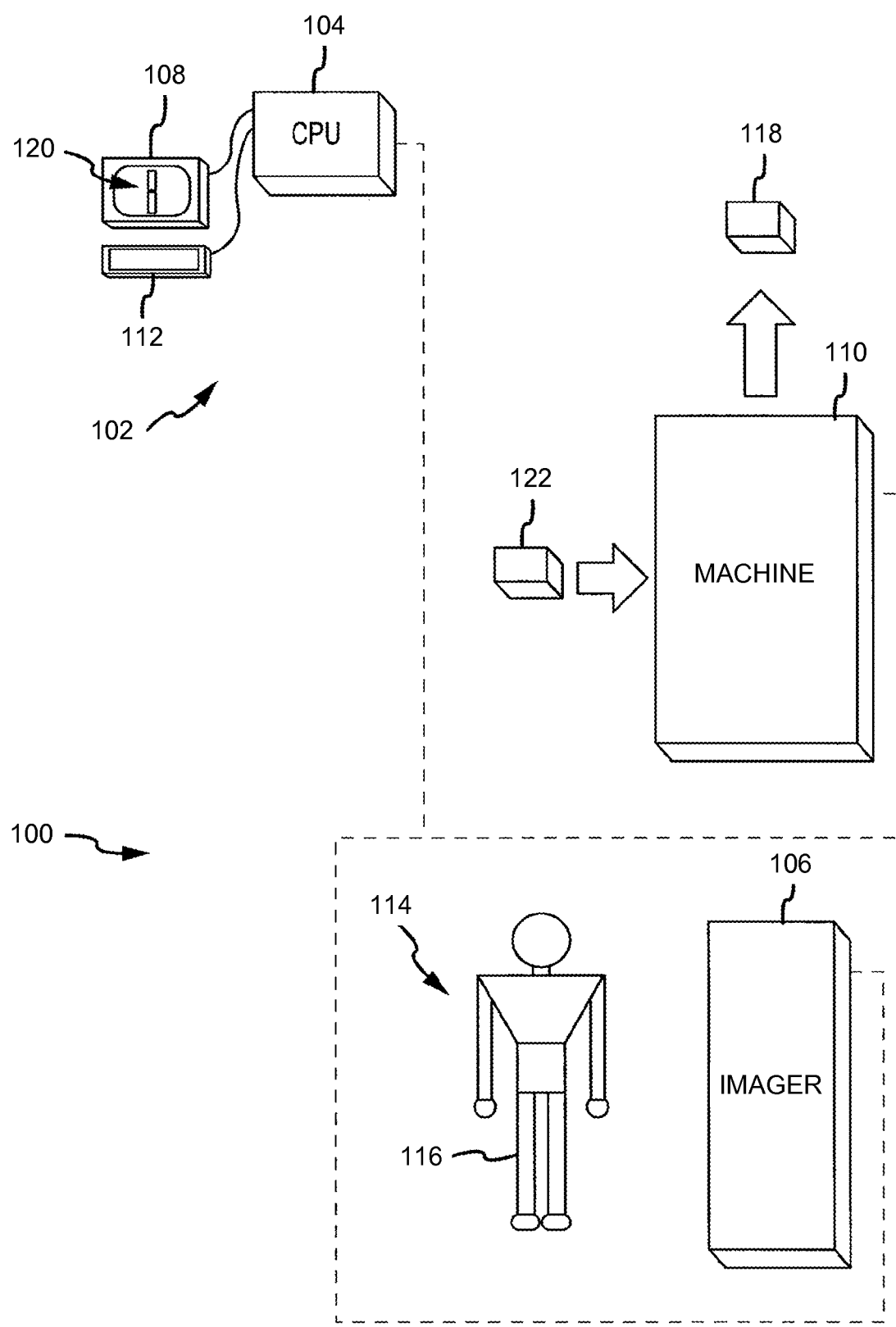
FIG. 1 is a schematic diagram of an example system for designing and manufacturing patient specific cutting guides based on anatomical model segmentation.

Referring to FIG. 1, an example system 100 for designing and manufacturing patient specific cutting guides based on anatomical model segmentation is shown. In one implementation, the system 100 includes a computing device 102, an imager 106, and a machining system 110. The computing device 102 is generally any form of computing device, such as a personal computer, work station, terminal, portable computer, mobile device, tablet, multimedia console, or the like. In one implementation, the computing device 102 includes at least one processor 104, a display 108, and operator interface controls 112. The imager 106 may be any form of medical imaging machine or device, including, but not limited to, a magnetic resonance imaging ("MRI") machine and a computed tomography ("CT") machine. The machine system 110 is generally any form of manufacturing machine, including, without limitation, a computer numerical control ("CNC") milling machine, a Stereolithography ("SLA") machine, or other machines configured to manufacture custom arthroplasty jigs, implants, or other custom medical apparatuses.

In one implementation, the computing device 102, the imager 106, and/or the machining system 110 are connected via a network. One or more other computing or data storage devices (e.g., one or more databases) may also be connected to the network. In another implementation, the computing device 102, the imager 106, and/or the machining system 110 are directly connected or are otherwise in communication. In still another implementation, the computing device 102, the imager 106, and/or the machining system 110 are separate systems.

As can be understood from FIG. 1, a patient 114 has a joint 116 (e.g., a knee, elbow, ankle, wrist, hip, shoulder, spine, cranial, or other joint) to be treated. The imager 106 generates a plurality of scans of the joint 116. Each of the scans corresponds to a thin slice of the joint 116. From the plurality of scans, the imager 106 or another computing device generates a plurality of two-dimensional ("2D") images of the joint 116.

The computing device 102 presents a user interface 120 generated by the processor 104 on the display 108. In one implementation, the computing device generates an anatomically accurate 3D model of the joint 116 using the 2D images and displays the 3D model on the user interface 120. As described in more detail herein, the anatomically accurate 3D model is generated based on segmentation splines in sagittal slices of a volumetric image of the joint 116, and the anatomically accurate 3D model of the joint 116 includes anatomically accurate segmentation splines. The computing device 102 transforms anatomically accurate segmentation splines into mating surface contours using surface smoothing and image quality compensation rules and algorithms. In one implementation, the computing device 102 modifies the mating surface contours to accommodate imaging deficiencies, manufacturing constraints, and/or surgical constraints. The computing device 102 smooths the mating surface contours in all 3D cross-sections in a manner that does not impinge on actual underlying surfaces of the bone, cartilage, or osteophytes in the joint 116. Stated differently, the computing device 102 generates a smooth mating surface model of arthroplasty target areas of the joint 116. The smooth mating surface model may be presented and interacted with on the user interface 120, for example, during pre-operative planning for an arthroplasty procedure that will use arthroplasty implants to restore the joint 116 to its pre-degenerated state or, in other words, its natural alignment state.

The computing device 102 generates manufacturing instructions for the production of customized arthroplasty jigs and outputs the manufacturing instructions to the machining system 110. In one implementation, the machining system 110 manufactures customized arthroplasty jigs 118 from blank jigs 122 provided to the machining system 110 based on the manufacturing instructions. In another implementation, the machining system 110 manufactures the customized arthroplasty jigs 118 using additive manufacturing or 3D printing techniques based on the manufacturing instructions. The customized arthroplasty jigs 118 are configured to matingly receive the arthroplasty target areas of the respective bones in the joint 116 to prepare the arthroplasty target areas in the joint 116 to receive arthroplasty joint implants, which are configured to restore the joint 116 to the pre-degenerated state.

Figure 2B:
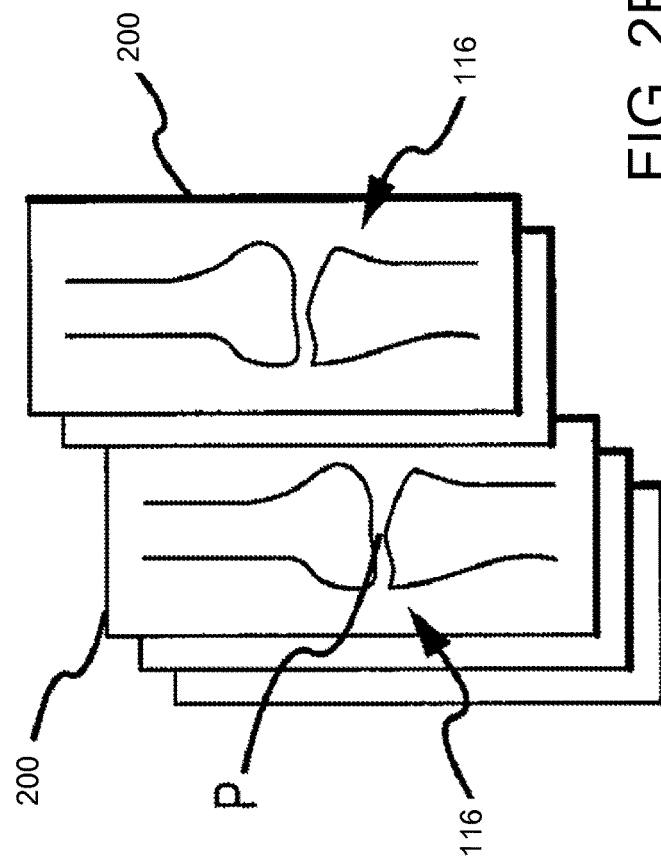
FIGS. 2A and 2B each illustrate two-dimensional images of a patient's joint, with FIG. 2B identifying a Point P for locating and creating a three-dimensional model.
Figure 2A:
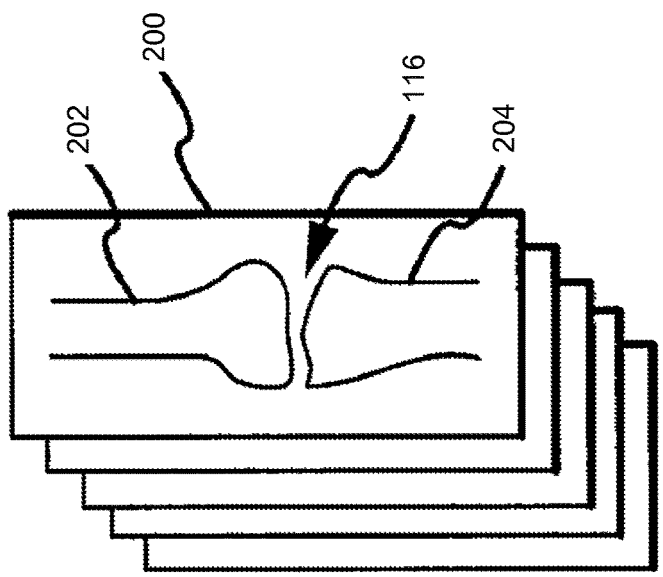

For a detailed description of generating a plurality of 2D images 200 of the joint 116 for locating and creating a 3D model of the joint 116, reference is made to FIGS. 2A and 2B. In on implementation, the plurality of scans captured by the imager 106 are used to generate the 2D images 200. For example, where the joint 116 is a knee, the 2D images include images of the femur 202 and/or the tibia 204. In one implementation, the 2D images are generated using an MRI machine using processes similar to those disclosed in U.S. patent application Ser. No. 11/946,002, entitled "Generating MRI Images Usable for the Creation of 3D Bone Models Employed to Make Customized Arthroplasty Jigs" and filed Nov. 27, 2007, which is hereby incorporated by reference in its entirety into the present application.

As can be understood from FIG. 2B, in one implementation, a point P is identified in the 2D images 200. The point P may be at the approximate medial-lateral and anterior-posterior center of the patient's joint 116, or the point P may be at any other location in the 2D images 200, including anywhere on, near or away from the bones 202 and 204 or the joint 116 formed by the bones 202 and 204. In one implementation, the point P may be used to locate 3D models created from the 2D images 200 and to integrate information generated via the 3D models. Point P, which serves as a position and/or orientation reference, may be a single point, two points, three points, a point plus a plane, a vector, etc., so long as the point P can be used to position and/or orient the 3D models generated via the 2D images 200.

Figure 3A:
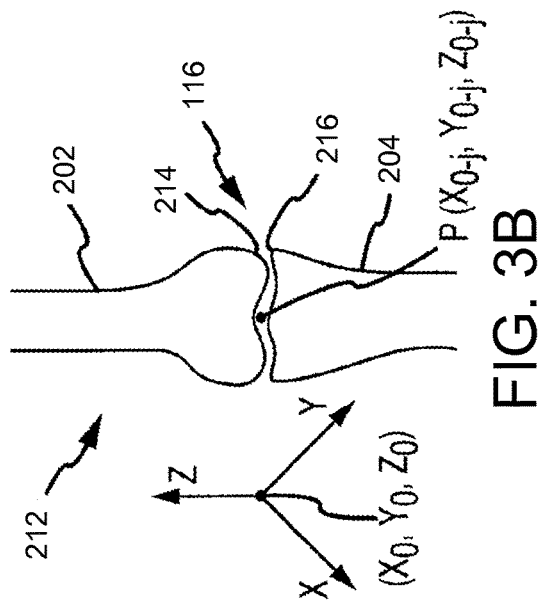
FIGS. 3A-3D show three-dimensional bone models of the bones forming the patient's joint generated using the two-dimensional images of FIGS. 2A and 2B.

Turning to FIGS. 3A-3D and FIG. 4, a detailed description of example operations 300 for determining saw cut locations and drill hole locations in the patient's bones allowing arthroplasty joint implants to generally restore the patient's joint line to its pre-degenerative alignment is provided. In one implementation, a generating operation 302 generates 3D bone models 206 (i.e., bone-only models) of the bones 202, 204 forming the patient's joint 116 generated using the 2D images 200. In one implementation, the bone models 206 depict the bones 202, 204 in the present deteriorated condition with their respective degenerated joint surfaces 208, 210, which may be a result of osteoarthritis, injury, a combination thereof, etc. The generating operation 302 may utilize various programs for creating the 3D bone models 206 from the 2D images 200 including, without limitation: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; Paraview available at www.paraview.org; and the like. As shown in FIG. 3A, a locating operation 304 locates the bone models 206, such that the point P is at coordinates $(X_{0-j}, Y_{0-j}, Z_{0-j})$ relative to an origin $(X_0, Y_0, Z_0)$ of an X-Y-Z axis.

Figure 3B:
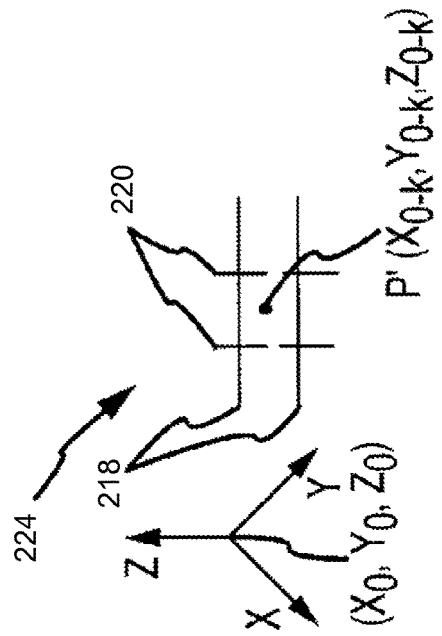

As indicated in FIG. 3B, a restoring operation 306 uses the 3D bone models 206 to create 3D "restored bone models" or "planning bone models" 212, wherein the degenerated surfaces 208, 210 are modified or restored to approximately their respective conditions prior to degeneration. Thus, the bones 202, 204 of the restored bone models 212 are reflected in approximately their condition prior to degeneration. The restored bone models 212 are located such that the point P is at coordinates $(X_{0-j}, Y_{0-j}, Z_{0-j})$ relative to the origin $(X_0, Y_0, Z_0)$. Thus, the restored bone models 212 share the same orientation and positioning relative to the origin $(X_0, Y_0, Z_0)$ as the bone models 206.

In one implementation, the restoring operation 306 manually creates the restored bone models 212 from the bone models 206 using the user interface 120 generated by the processor 104 of the computing device 102 based on an extent the degenerated surfaces 208, 210 surfaces on the 3D bone models 206 need to be modified to restore them to their pre-degenerated condition. By interacting with the user interface 120, the 3D degenerated surfaces 208, 210 may be manipulated to restore the surfaces 208, 210 to a state representing the pre-degenerated condition. The result of this manual restoration process is the 3D restored bone models 212, wherein surfaces 214, 216 are indicated in a non-degenerated state.

In another implementation, restoring operation 306 is generally or completely automated. In other words, a modeling application executed by the processor 104 analyzes the bone models 206 and their degenerated surfaces 208, 210 to determine how and to what extent the degenerated surfaces 208, 210 surfaces on the 3D bone models 206 need to be modified to restore them to their pre-degenerated condition. The modeling application then manipulates the 3D degenerated surfaces 208, 210 to restore the surfaces 208, 210 to a state intended to represent the pre-degenerated condition. The result of this automated restoration process is the 3D restored bone models 212, wherein the surfaces 214, 216' are indicated in a non-degenerated state.

Figure 3C:
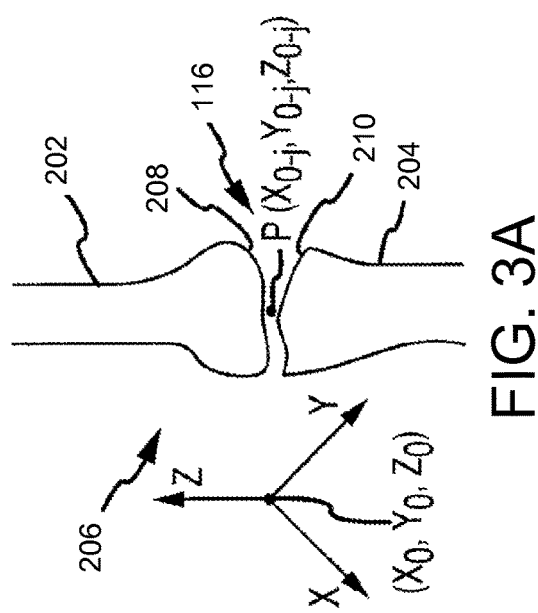

As depicted in FIG. 3C, a shaping operation 308 employs the restored bone models 212 in a pre-operative planning ("POP") procedure to determine saw cut locations 218 and drill hole locations 220 in the patient's bones 202, 204 that will allow the arthroplasty joint implants to generally restore the patient's joint line to it pre-degenerative alignment.

In one implementation, the shaping operation 308 is manual, wherein 3D implant models 222 (e.g., femur and tibia implants in the context of the joint being a knee) and the restored bone models 212 are manually manipulated relative to each other using the user interface 120 generated by the processor 104 of the computing device 102. By superimposing the implant models 222 over the restored bone models 212, or vice versa, the joint surfaces of the implant models 222 can be aligned or caused to correspond with the joint surfaces of the restored bone models 212. By causing the joint surfaces of the models 212 and 222 to so align, the implant models 222 are positioned relative to the restored bone models 212, such that the saw cut locations 218 and drill hole locations 220 can be determined relative to the restored bone models 212. In another implementation, the shaping operation 308 is generally or completely automated. For example, a modeling application executed by the processor 104 manipulates the 3D implant models 222 and the restored bone models 212 relative to each other to determine the saw cut locations 218 and the drill hole locations 220 relative to the restored bone models 212.

Figure 3D:
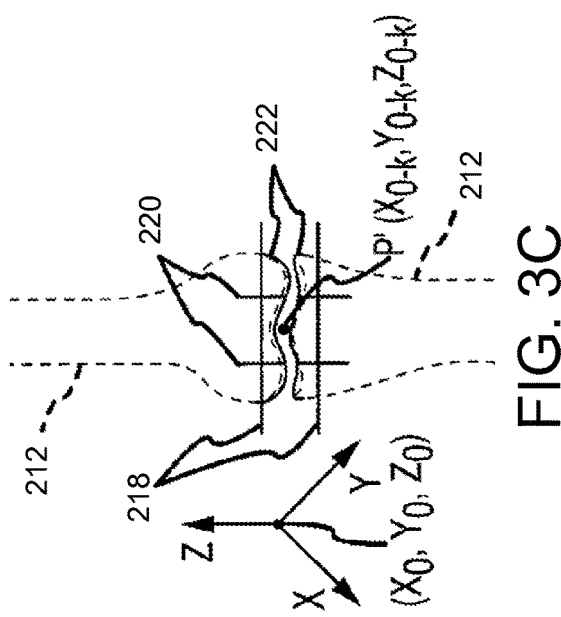
Figure 6:
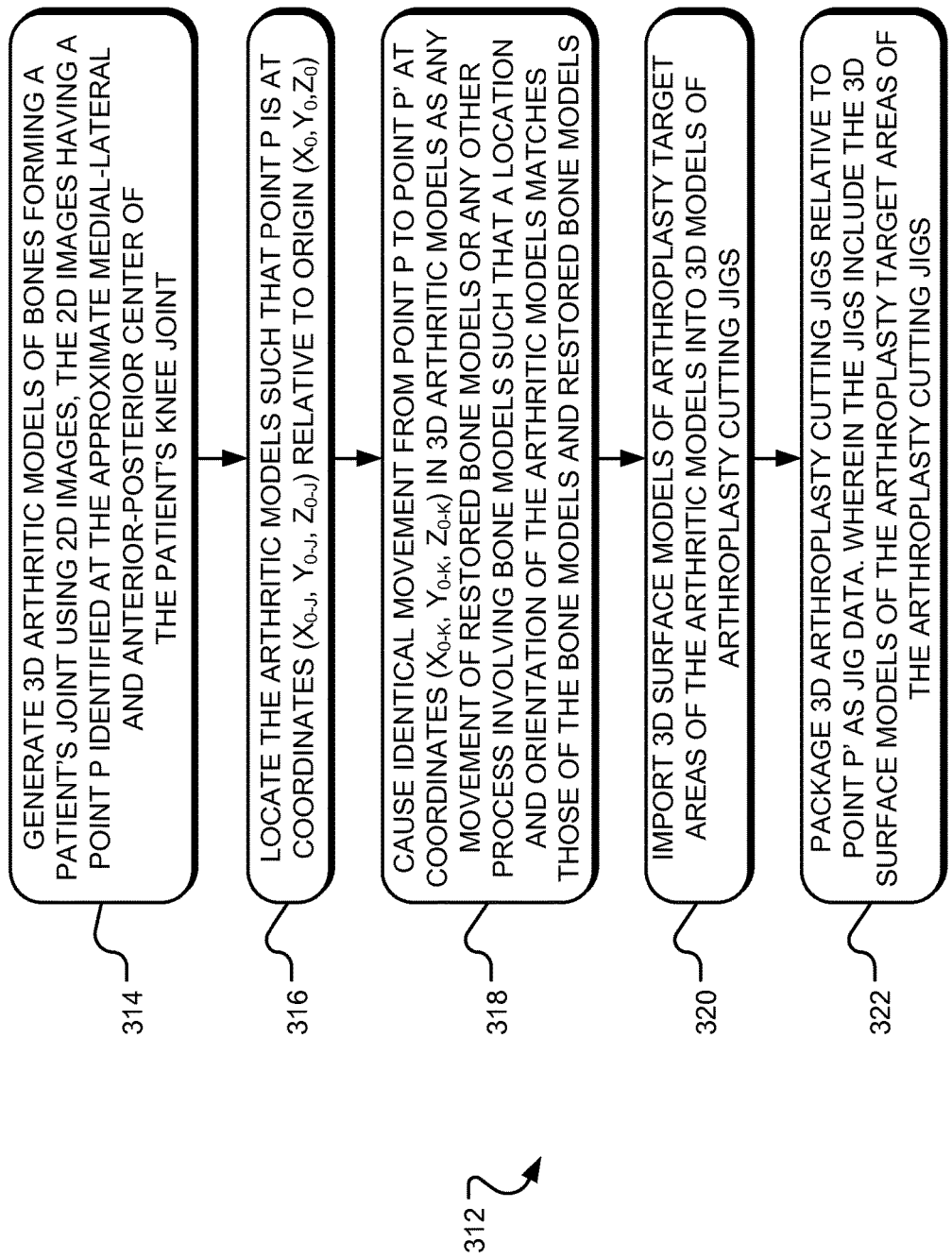
FIG. 6 illustrates example operations for generating three-dimensional mating surface models of arthroplasty target areas of the arthroplasty cutting jigs.

The shaping operation 308 superimposes the implant models 222 over the restored bone models 212, or vice versa. In one implementation, the implant models 222 are located at a point P' $(X_{0-k}, Y_{0-k}, Z_{0-k})$ relative to the origin $(X_0, Y_0, Z_0)$, and the restored bone models 212 are located at the point P $(X_{0-j}, Y_{0-j}, Z_{0-j})$. To cause the joint surfaces of the models 212 and 222 to correspond, the modeling application may move the restored bone models 212 from the point P $(X_{0-j}, Y_{0-j}, Z_{0-j})$ to the point P' $(X_{0-k}, Y_{0-k}, Z_{0-k})$, or vice versa. Once the joint surfaces of the models 212 and 222 are in close proximity, the joint surfaces of the implant models 222 may be shape-matched to align or correspond with the joint surfaces of the restored bone models 212. By causing the joint surfaces of the models 212 and 220 to so align, the implant models 222 are positioned relative to the restored bone models 212 such that the saw cut locations 218 and drill hole locations 220 can be determined relative to the restored bone models 212. As indicated in FIG. 3D, in one implementation, a packaging operation 310 packages or otherwise consolidates data regarding the saw cut locations 218 and the drill hole locations 220 relative to the point P' $(X_{0-k}, Y_{0-k}, Z_{0-k})$ into "saw cut and drill hole data" 224.

For a detailed description of example operations 312 for generating 3D mating surface models of arthroplasty target areas of the arthroplasty cutting jigs, reference is made to FIGS. 5A-5C and FIG. 6.

As can be understood from FIG. 5A, a generating operation 314 generates 3D bone and cartilage models (i.e., "arthritic models") 226 of the bones 202, 204 forming the patient's joint 116 using the 2D images 200. The generating operation 314 may utilize various programs for creating the 3D computer generated arthritic models 226 from the 2D images 200 including, without limitation: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; Paraview available at www.paraview.org; or the like.

A locating operation 316 locates the arthritic models 226, such that the point P is at coordinates $(X_{0-j}, Y_{0-j}, Z_{0-j})$ relative to the origin $(X_0, Y_0, Z_0)$ of the X-Y-Z axis. Thus, the bone and arthritic models 206 and 226 share the same location and orientation relative to the origin $(X_0, Y_0, Z_0)$. This position/orientation relationship is generally maintained. Accordingly, movements relative to the origin $(X_0, Y_0, Z_0)$ of the bone models 206 and the various descendants thereof (i.e., the restored bone models 212, bone cut locations 218 and drill hole locations 220) are also applied to the arthritic models 226 and the various descendants thereof (i.e., jig models 228). Maintaining the position/orientation relationship between the bone models 206 and arthritic models 226 and their respective descendants allows the "saw cut and drill hole data" 224 to be integrated into "jig data" 234 to form "integrated jig data" 236 employed by the machining system 110 to manufacture the customized arthroplasty jigs 118, described with respect to FIGS. 7-9B.

Similar to the bone models 206, the arthritic models 226 depict the bones 202, 204 in the present deteriorated condition with their respective degenerated joint surfaces 208, 210, which may be a result of osteoarthritis, injury, a combination thereof, etc. However, unlike the bone models 206, the arthritic models 226 are not bone-only models, but include cartilage in addition to bone. Accordingly, the arthritic models 226 depict arthroplasty target areas 232 generally as they will exist when the customized arthroplasty jigs 118 matingly receive the arthroplasty target areas 232 during the arthroplasty surgical procedure.

As indicated in FIG. 5B and already mentioned above, to coordinate the positions/orientations of the bone and arthritic models 206, 226 and their respective descendants, a positioning operation 318 tracks any movement of the restored bone models 212 from point P to point P' and causes a generally identical displacement for the arthritic models 226. As depicted in FIG. 5B, an importing operation 320 imports 3D surface models 230 of the arthroplasty target areas 232 of the arthritic models 226 into 3D arthroplasty jig models 228. Thus, the jig models 228 are configured or indexed to matingly receive the arthroplasty target areas 232 of the arthritic models 226. The jigs 118 manufactured to match such jig models 228 will then matingly receive the arthroplasty target areas of the actual joint bones in the joint 116 during the arthroplasty surgical procedure.

In some implementations, the 3D surface models 230 may be modified to account for irregularities in the patient's bone anatomy or limitations in the imaging process. For example, the 3D surface models 230 may be subjected to, or the result of, an "overestimation" process. The "overestimated" 3D surface models 230 may result in bone mating surfaces of the actual jigs that matingly receive and contact certain portions of the arthroplasty target areas of the actual joint bones while other portions of the jigs are spaced apart from the bones, including, for example, some regions of the arthroplasty target areas of the actual joint bones. Thus, the bone mating surfaces of the actual jigs may matingly contact certain specific portions of the arthroplasty target areas of the actual joint bones while other areas of the arthroplasty target areas are not matingly contacted. In some implementations, the specific portions of the arthroplasty target areas contacted by the jig's bone mating surfaces may be those areas that are most likely to be accurately 3D computer modeled and most likely to result in a reliably accurate mating contact between the jig's bone mating surface and the arthroplasty target areas, and the portions of the arthroplasty target areas not contacted by the jig's bone mating surfaces may be those areas that are the least likely to be accurately 3D computer modeled.

In other words, for some implementation, overestimation may result in areas of mating contact for the bone mating surfaces of the actual jigs being based on the areas of the 3D surface models 230 that are most reliably accurate with respect to the image scan data and most readily machined via the tooling of the machining system 110. Conversely, for some implementations, overestimation may result in areas of non-contact for the bone mating or other surfaces of the actual jigs for those areas of the jig pertaining to those areas of the 3D surface models 230 that result from image scan data that is less accurate or reliable and/or represent bone features that are too small to be readily machined via the tooling of the machining system 110. The systems and methods of overestimation may be similar to those disclosed in U.S. patent application Ser. No. 12/505,056, entitled "System and Method for Manufacturing Arthroplasty Jigs having Improved Mating Accuracy" and filed Jul. 17, 2009, which is incorporated by reference in its entirety into the present application. The mating surface contours in all 3D cross-sections of the 3D surface models 230 are smoothed in a manner that does not impinge on actual underlying surfaces of the bone 208, 210. The result of this process is actual jigs with a bone mating surfaces that matingly contact certain reliable regions of the arthroplasty target areas of the actual joint bones while avoiding contact with certain less reliable regions of the arthroplasty target areas, resulting in jigs with bone mating surfaces that accurately and reliably matingly receive the arthroplasty target regions.

In one implementation, the importing operation 320 for indexing the jig models 228 to the arthroplasty target areas 232 is manual. The 3D models 226 and 228 are manually manipulated relative to each other using the user interface 120 generated by the processor 104. In one implementation, by superimposing the jig models 228 (e.g., femur and tibia arthroplasty jigs in the context of the joint being a knee) over the arthroplasty target areas 232 of the arthritic models 226, or vice versa, the surface models 230 of the arthroplasty target areas 232 can be imported into the jig models 228, resulting in jig models 228 indexed to matingly receive the arthroplasty target areas 232 of the arthritic models 226. The Point P' $(X_{0-k}, Y_{0-k}, Z_{0-k})$ can also be imported into the jig models 228, resulting in the jig models 228 positioned and oriented relative to the point P' ($X_{0-k}$, $Y_{0-k}$, $Z_{0-k}$) to allow their integration with the bone cut and drill hole data 224.

In another implementation, the importing operation 320 for indexing the jig models 228 to the arthroplasty target areas 232 is generally or completely automated. For example, the importing operation 320 may create 3D surface models 230 of the arthroplasty target areas 232 of the arthritic models 226 using an application generated by the processor 104. The importing operation 320 may then import the surface models 230 and the point P' ($X_{0-k}$, $Y_{0-k}$, $Z_{0-k}$) into the jig models 228, resulting in the jig models 228 being indexed to matingly receive the arthroplasty target areas 232 of the arthritic models 226. In some implementations, the surface models 230 may include accounting for irregularities in the patient's bone anatomy and/or limitations in the imaging technology by creating deliberate gaps between the jig's surface and the patient's bone. The resulting jig models 228 are also positioned and oriented relative to the point P' ($X_{0-k}$, $Y_{0-k}$, $Z_{0-k}$) to allow their integration with the bone cut and drill hole data 224.

In one implementation, the arthritic models 226 may be 3D volumetric models as generated from the closed-loop process discussed herein. In other implementations, the arthritic models 226 may be 3D surface models as generated from the open-loop process discussed herein. As indicated in FIG. 5C, in one implementation, a packaging operation 322 packages or otherwise consolidates data regarding the jig models 228 and the surface models 230 relative to the point P' ($X_{0-k}$, $Y_{0-k}$, $Z_{0-k}$) as the "jig data" 234.

Figure 7:
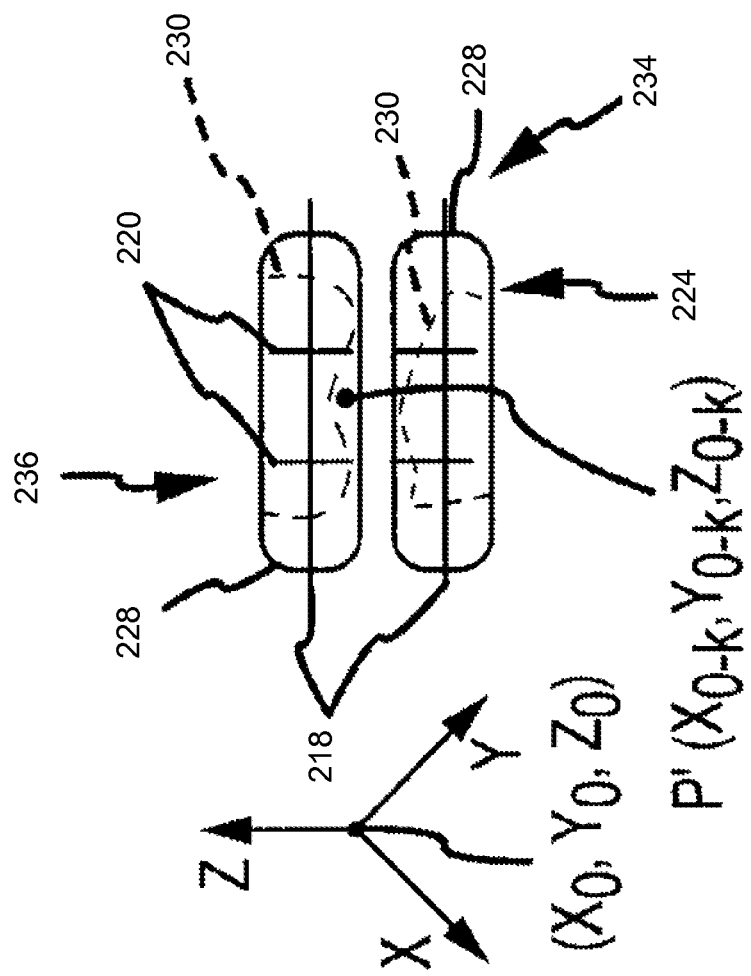
FIG. 7 shows a three-dimensional model of the patient's joint including integrated jig data generated based on the bones models and arthritic models of FIGS. 3A-3D and FIGS. 5A-C, respectively.
Figure 8:
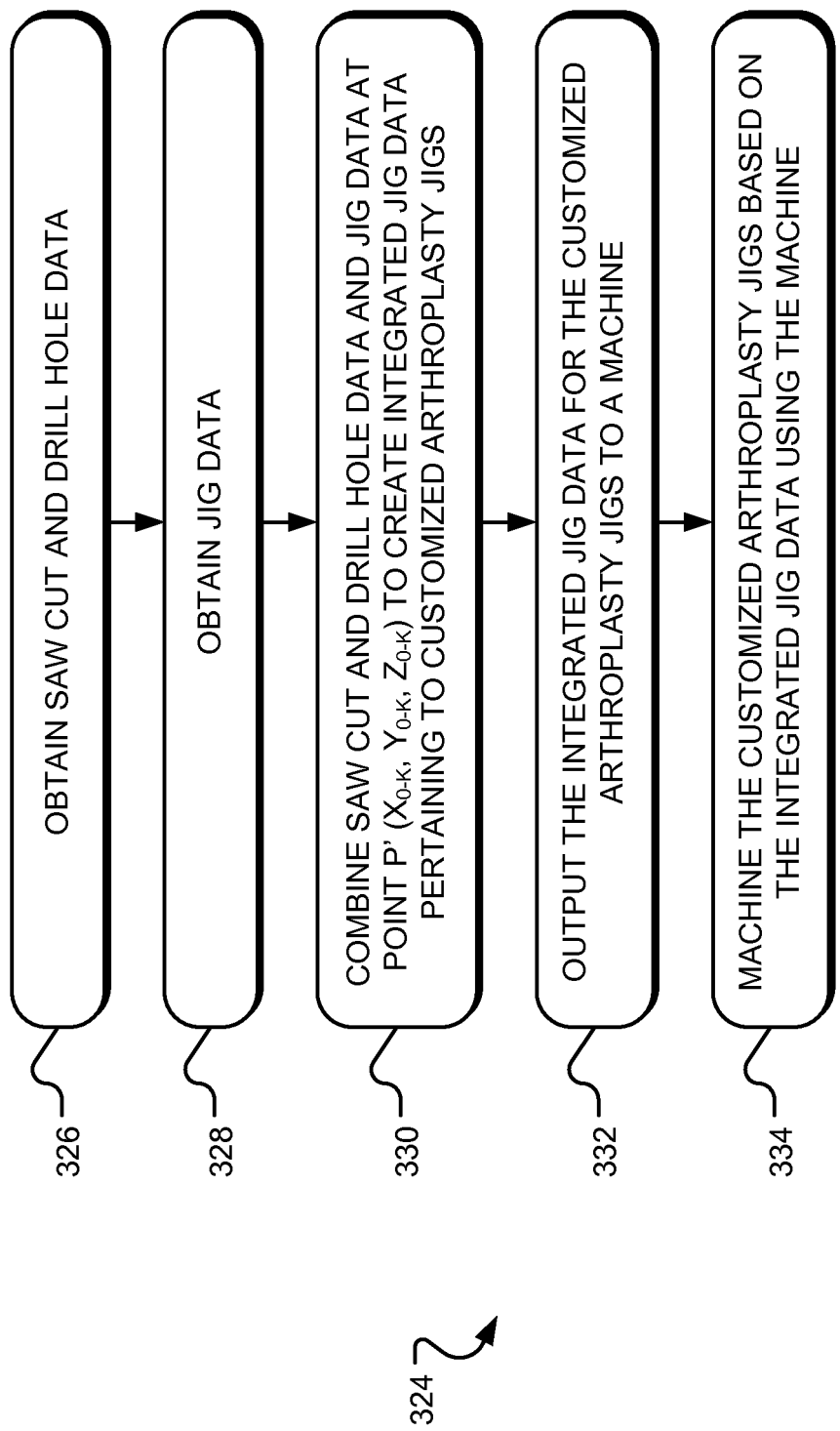
FIG. 8 illustrates example operations for machining customized arthroplasty jigs.

As can be understood from FIGS. 7-8, which illustrate example operations 324 for machining customized arthroplasty jigs 118, in one implementation, a first obtaining operation 326 obtains the "saw cut and drill hole data" 224, and a second obtaining operation 328 obtains the "jig data" 234. A combining operation 330 integrates the "saw cut and drill hole data" 224 with the "jig data" 234 to generate the "integrated jig data" 236. As explained above, since the "saw cut and drill hole data" 224, "jig data" 234, and their various ancestors (e.g., models 206, 212, 226, 228) are matched to each other for position and orientation relative to the points P and P', the "saw cut and drill hole data" 224 is properly positioned and oriented relative to the "jig data" 234 for proper integration into the "jig data" 234. The resulting "integrated jig data" 236, when provided to the machining system 110, results in jigs 118: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated or natural alignment state. In one implementation, in outputting 332 outputs the "integrated jig data" 236 to the machining system 110. A machining operation 334 machines the customized arthroplasty jigs 118 based on the "integrated jig data" 236 using the machining system 110.

Figure 9B:
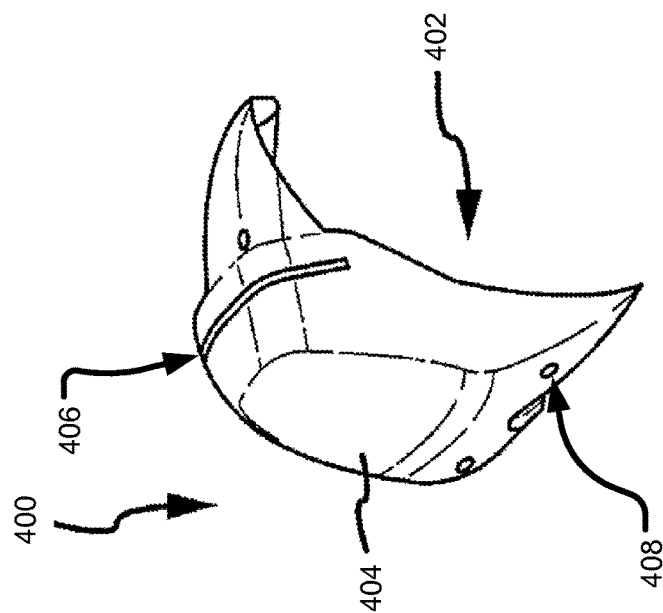
FIGS. 9A and 9B are bottom and top isometric views of an example custom fit or mating femur arthroplasty cutting guide.
Figure 9A:
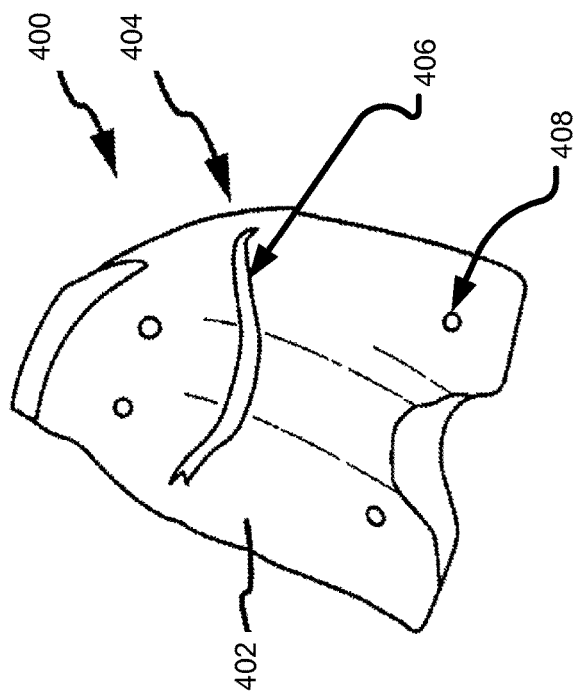

For a discussion of example customized arthroplasty cutting jigs 118 capable of being manufactured via the above-discussed process, reference is made to FIGS. 9A and 9B. While, as pointed out above, the above-discussed process may be employed to manufacture jigs 118 configured for arthroplasty procedures involving knees, elbows, ankles, wrists, hips, shoulders, vertebra interfaces, etc., the jig examples depicted in FIGS. 9A and 9B are for TKR procedures. Thus, FIGS. 9A and 9B are, respectively, bottom and top perspective views of an example customized arthroplasty femur jig 400.

As indicated in FIGS. 9A and 9B, the femur arthroplasty jig 400 may include an interior side or portion 402 and an exterior side or portion 404. When the femur cutting jig 400 is used in a TKR procedure, the interior side or portion 402 faces and matingly receives the arthroplasty target area 232 of the femur lower end, and the exterior side or portion 404 is on the opposite side of the femur cutting jig 400 from the interior portion 402. The interior portion 402 of the femur jig 400 is configured to match the surface features of the damaged lower end (i.e., the arthroplasty target area 232) of the patient's femur 202. Thus, when the target area 232 is received in the interior portion 402 of the femur jig 400 during the TKR surgery, the surfaces of the target area 232 and the interior portion 402 match. In one implementation, the femur jig 400 includes saw cut features (including a resection slot 406) and drill hole features 408 defined therein that correspond to the saw cut locations 218 and the drill hole locations 220.

In one implementation, the surface of the interior portion 402 of the femur cutting jig 400 is machined or otherwise formed into a selected femur jig blank 122 and is based or defined off of a 3D surface model 230 of a target area 232 of the damaged lower end or target area 232 of the patient's femur 202. In some implementations, the 3D surface model 230 may modified via the "overestimation" process described herein to account for limitations in the medical imaging process and/or limitations in the machining process. Further, mating surface contours in all 3D cross-sections of the 3D surface models 230 are smoothed in a manner that does not impinge on actual underlying surfaces of the bone 208, 210, as described herein.

Turning to FIGS. 10A to 12, a detailed description of example operations 600 for generating a 3D model 230 of a target area 232 of a damaged lower end 500 of the patient's femur 202 to produce the customized arthroplasty jig 118 is provided.

In one implementation, an obtaining operation 602 obtains a plurality of image slices 200 generated using the imager 106. FIG. 10A is an anterior-posterior ("AP") image slice 502 of the damaged lower or knee joint end 500 of the patient's femur 202, wherein the image slice 502 includes an open-loop contour line segment 504 corresponding to the target area 232 of the damaged lower end 500. FIG. 10B is a plurality of image slices (200-1, 200-2, . . . 200-n) with their respective open-loop contour line segments (504-1, 504-2, . . . 504-n), the open-loop contour line segments 504 being accumulated to generate the 3D model 230 of the target area 232. FIG. 10O is a 3D model 230 of the target area 232 of the damaged lower end 500 as generated using the open-loop contour line segments (200-1, 200-2, . . . 200-n) depicted in FIG. 10B. FIGS. 11A-C are respectively similar to FIGS. 10A-10C, except FIGS. 11A-110 pertain to a closed-loop contour line as opposed to an open-loop contour line.

As can be understood from FIG. 10A, the imager 106 generates a 2D image slice 200 of the damaged lower or knee joint end 500 of the patient's femur 202. As depicted in FIG. 10A, the 2D image 200 may be an AP view of the femur 202. Depending on whether the imager 106 is a MRI, a CT imager, or other imager, the image slice 200 will be a MRI slice, a CT slice, or other image slice. The damaged lower end 500 includes the posterior condyle 506, an anterior femur shaft surface 508, and an area of interest or targeted area 232 that extends from the posterior condyle 506 to the anterior femur shaft surface 508. The targeted area 232 of the femur lower end may be the articulating contact surfaces of the femur lower end that contact corresponding articulating contact surfaces of the tibia upper or knee joint end.

As shown in FIG. 10A, the image slice 200 may depict the cancellous bone 510, the cortical bone 512 surrounding the cancellous bone 510, and the articular cartilage lining portions of the cortical bone 512. The contour line 504 may extend along the targeted area 232 and immediately adjacent the cortical bone 512 and cartilage to outline the contour of the targeted area 232 of the femur lower end 500. The contour line 504 extends along the targeted area 232 starting at point A on the posterior condyle 506 and ending at point B on the anterior femur shaft surface 508.

In one implementation, as indicated in FIG. 10A, the contour line 504 extends along the targeted area 232 but not along the rest of the surface of the femur lower end 500. As a result, the contour line 504 forms an open-loop that, as will be discussed with respect to FIGS. 10B and 102C, can be used to form an open-loop region or 3D model 230, which is discussed with respect to the importing operation 320 and closely matches the 3D surface of the targeted area 232 of the femur lower end 500. Thus, in one implementation, the contour line 504 is an open-loop and does not outline the entire cortical bone surface of the femur lower end 500. Also, in one implementation, the open-loop process is used to form a 3D surface model from the 3D images 200 that generally takes the place of the arthritic model 226 discussed above and which is used to create the 3D surface model 230 used in the creation of the "jig data" 234.

Turning to FIGS. 11A to 11O, in one implementation and in contrast to the open-loop contour line 504 depicted in FIGS. 10A and 10B, the contour line is a closed-loop contour line 514 that outlines the entire cortical bone surface of the femur lower end 500 and results in a closed-loop area, as depicted in FIG. 11A. The closed-loop contour lines 514-2, . . . 514-n of each image slice 200-1, . . . 200-n are combined, as indicated in FIG. 11B. A closed-loop area may require the analysis of the entire surface region of the femur lower end 500 and result in the formation of a 3D model 230 of the entire femur lower end 500 as illustrated in FIG. 11O. Thus, the 3D surface model 230 resulting from the closed-loop process ends up having in common much, if not all, the surface of the 3D arthritic model 226. In one implementation, the closed-loop process may result in a 3D volumetric anatomical joint solid model from the 2D images 200 via applying mathematical algorithms. U.S. Pat. No. 5,682,886, which was filed Dec. 26, 1995 and is incorporated by reference in its entirety herein, applies a snake algorithm forming a continuous boundary or closed-loop. After the femur 202 has been outlined, a modeling process is used to create the 3D surface model 230, for example, through a Bezier patches method. Other 3D modeling processes are applicable to 3D surface model generation for closed-loop, volumetric solid modeling.

In one implementation, the closed-loop process is used to form a 3D volumetric solid model that is essentially the same as the arthritic model 226 from the 3D images 200. An example of a closed-loop methodology is disclosed in U.S. patent application Ser. No. 11/641,569 to Park, entitled "Improved Total Joint Arthroplasty System" and filed Jan. 19, 2007, which is incorporated by reference in its entirety herein. The 3D volumetric solid model is used to create the surface model 230 used in the creation of the "jig data" 236.

As can be understood from FIG. 10B, the obtaining operation 602 obtains a plurality of image slices (200-1, 200-2 . . . 200-n) generated via repetitive imaging operations by the imager 106. In one implementation, a generating operation 604 generates an open-loop contour line (504-1, 504-2 . . . 504-n) for each image slice 200 extending along the targeted region 232 in a manner as discussed above. In one implementation, each image slice 200 is a two-millimeter 2D image slice. The plurality of open-loop contour lines (504-1, 504-2, . . . 504-n) are smoothed. A compiling operation 606 compiles the plurality of 2D image slices (200-1, 200-2 . . . 200-n) and, more specifically, the plurality of smoothed open-loop contour lines (504-1, 504-2, . . . 504-n) into the 3D femur surface computer model 230 depicted in FIG. 10O. A similar process may be employed with respect to the closed-loop contour lines depicted in FIGS. 11A to 11O.

As can be understood from FIG. 10C, the 3D femur surface computer model 230 is a 3D computer representation of the targeted region 232 of the femur lower end 500. In one implementation, the 3D representation of the targeted region 232 is a 3D representation of the articulated tibia contact surfaces of the femur distal end 500. As the open-loop generated 3D model 230 is a surface model of the relevant tibia contacting portions of the femur lower end, as opposed to a 3D model of the entire surface of the femur lower end as would be a result of a closed-loop contour line, the open-loop generated 3D model 230 is less time and memory intensive to generate.

In one implementation, the open-loop generated 3D model 230 is a surface model of the tibia facing end face of the femur lower end 500, as opposed a 3D model of the entire surface of the femur lower end 500. The 3D model 230 can be used to identify the area of interest or targeted region 232, which, as previously stated, may be the relevant tibia contacting portions of the femur lower end 500. In some implementations, the open-loop generated 3D model 230 is less time and memory intensive to generate as compared to a 3D model of the entire surface of the femur distal end 500, as would be generated by a closed-loop contour line. However, the systems and methods disclosed herein may employ either the open-loop or closed-loop methodology and should not be limited to one or the other.

Regardless of whether the 3D model 230 is a surface model of the targeted region 232 (i.e., a 3D surface model generated from an open-loop process and acting as the arthritic model 206) or the entire tibia facing end face of the femur lower end 500 (i.e., a 3D volumetric solid model generated from a closed-loop process and acting as the arthritic model 206), the data pertaining to the contour lines 504 can be converted into the 3D contour computer model 230 via the surface rendering techniques disclosed in any of the aforementioned U.S. patent applications to Park. For example, surface rending techniques employed include point-to-point mapping, surface normal vector mapping, local surface mapping, and global surface mapping techniques. Depending on the situation, one or a combination of mapping techniques or surface rendering techniques can be employed as disclosed in U.S. patent application Ser. No. 12/505,056, entitled "System and Method for Manufacturing Arthroplasty Jigs having Improved Mating Accuracy" and filed Jul. 17, 2009.

Figure 13:
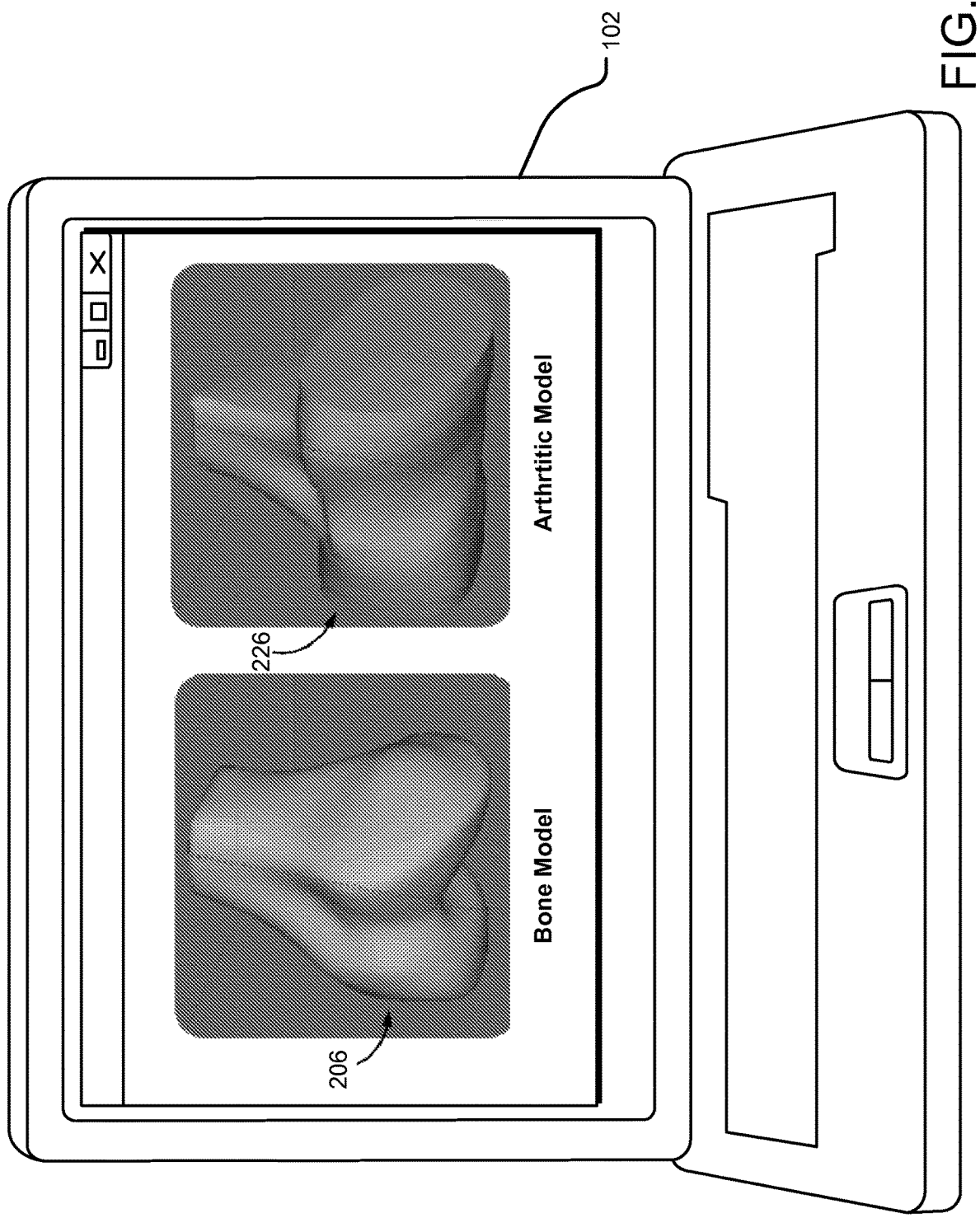
FIG. 13 shows an example user interface generated by a modeling application and displayed in a window of a computing device, the user interface displaying a three-dimensional bone model and a three-dimensional arthritic model of a patient's femur.

FIG. 13 shows an example of the user interface 120 generated by the processor 104 and displayed in a window shown on the display 108 of the computing device 102. As can be understood from FIG. 13, the user interface 120 displays the 3D bone model 206 and the 3D arthritic model 226 of the femur 202 of the patient 114. In one implementation, the 3D bone model 206 and the 3D arthritic model 226 are generated as described with respect to FIG. 2A to FIG. 6. As described herein, the 3D bone model 206 is a bone-only model of the femur 202 of the patient 114, representing the femur 202 without any cartilage and, in some cases, in an estimated configuration of the femur 202 in a pre-degenerative state. The 3D arthritic model 226 is a bone and cartilage model, as described herein, representing the femur 202 with cartilage and, in some cases, in an overestimated configuration wherein surfaces of the 3D arthritic model 226 are expanded outwardly in areas where the bone surface is difficult to model due to imaging limitations or the surface is difficult to replicate during manufacturing due to limitations in manufacturing techniques.

For a detailed discussion of an anatomical femur model 724 used for surgeon review and pre-operative planning with respect to the positioning of the customized arthroplasty femur jig 400 and a prosthetic implant 800, reference is made to FIGS. 14-30. As will be understood, in one implementation, a mating surface model 730 is generated from the anatomical femur model 724. The mating surface model 730 is used to define the mating surface 402 in the customized arthroplasty femur jig 400.

Figure 14:
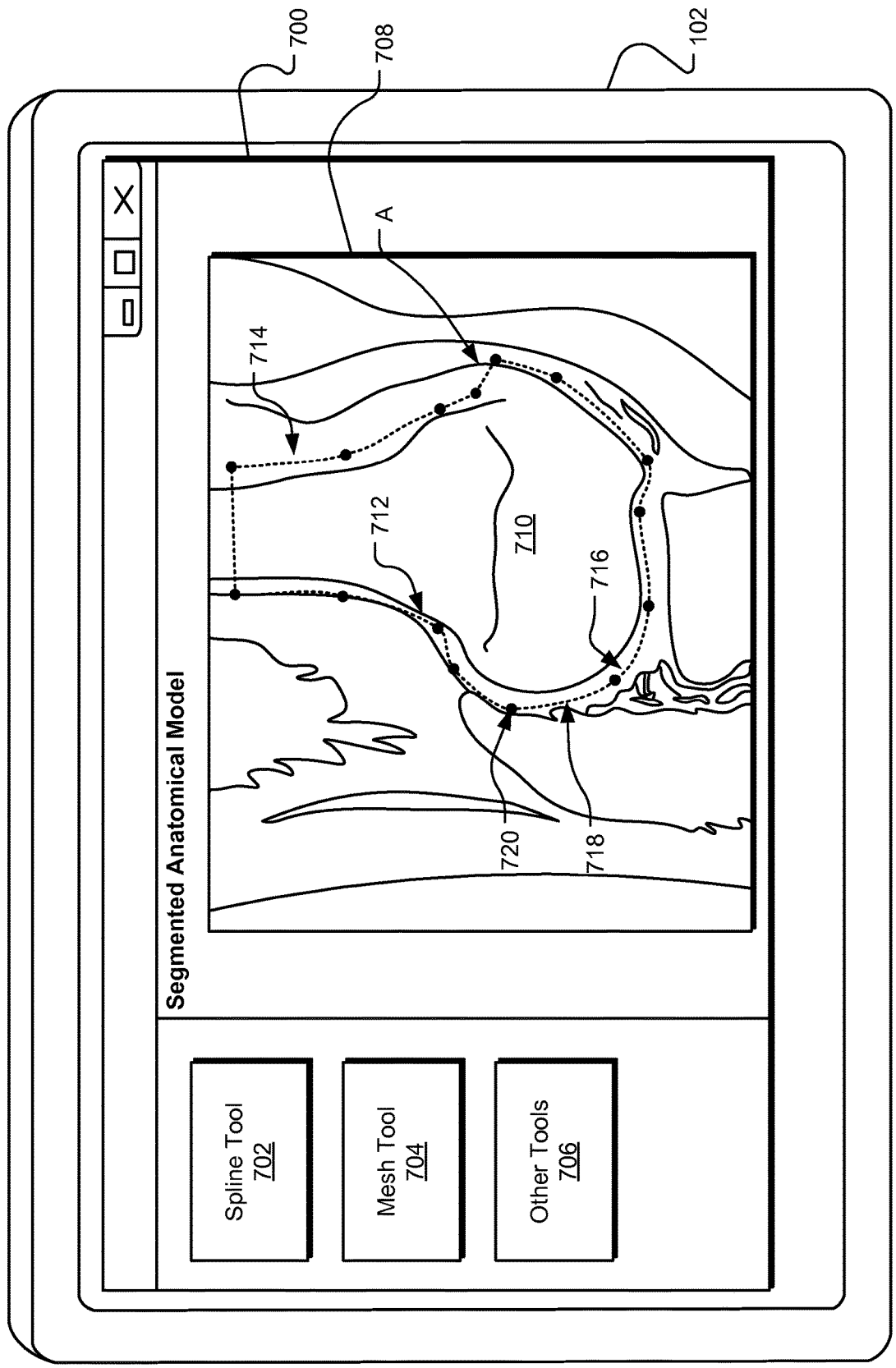
FIG. 14 illustrates the user interface displaying a sagittal image slice of the patient's femur, wherein the image slice is being segmented.

To begin the discussion of the generation of the anatomical femur model 724, reference is made to FIG. 14. In one implementation, the user interface 120 is generated by the processor 104 of the computing device 102 and is presented on the display 108 of the computing device. The various user interfaces 120 described herein may include a variety of tools, including, for example, a spline tool 702, a mesh tool 704, and other tools 706, which may be used to generate and otherwise interact with the models and data presented with the user interface 120. It will be appreciated that such depictions are exemplary only and not intended to be limiting.

As can be understood from FIG. 14, in one implementation, a segmented anatomical model user interface 700 is generated by the processor 104 of the computing device 102 and is presented on the display 108 of the computing device. The segmented anatomical model user interface 700 includes a sagittal image slice 708 of the patient's femur 710, wherein the image slice 708 is being segmented.

In one implementation, the spline tool 702 segments the image slice 708 along the actual outer bone surface, such that a segmenting spline 718 (shown in dashed lines) extends along an outer cortical bone surface 712 and an outer cartilage surface 716. The segmenting spline 718 and one or more control points 720 of the segmenting spline 718 also extend along an outer surface of osteophytes when such osteophytes are present on locations of the femur 710 other than locations near the femur shaft 714. Stated differently, in one implementation, the segmenting spline 718 outlines the femur 710, including the bones and cartilage, but cuts off osteophytes located near the femur shaft 714. For example, as shown in FIG. 14, as indicated at arrow A, the osteophytes near the femur shaft 714 are bisected by the segmenting spline 718.

Figure 15:
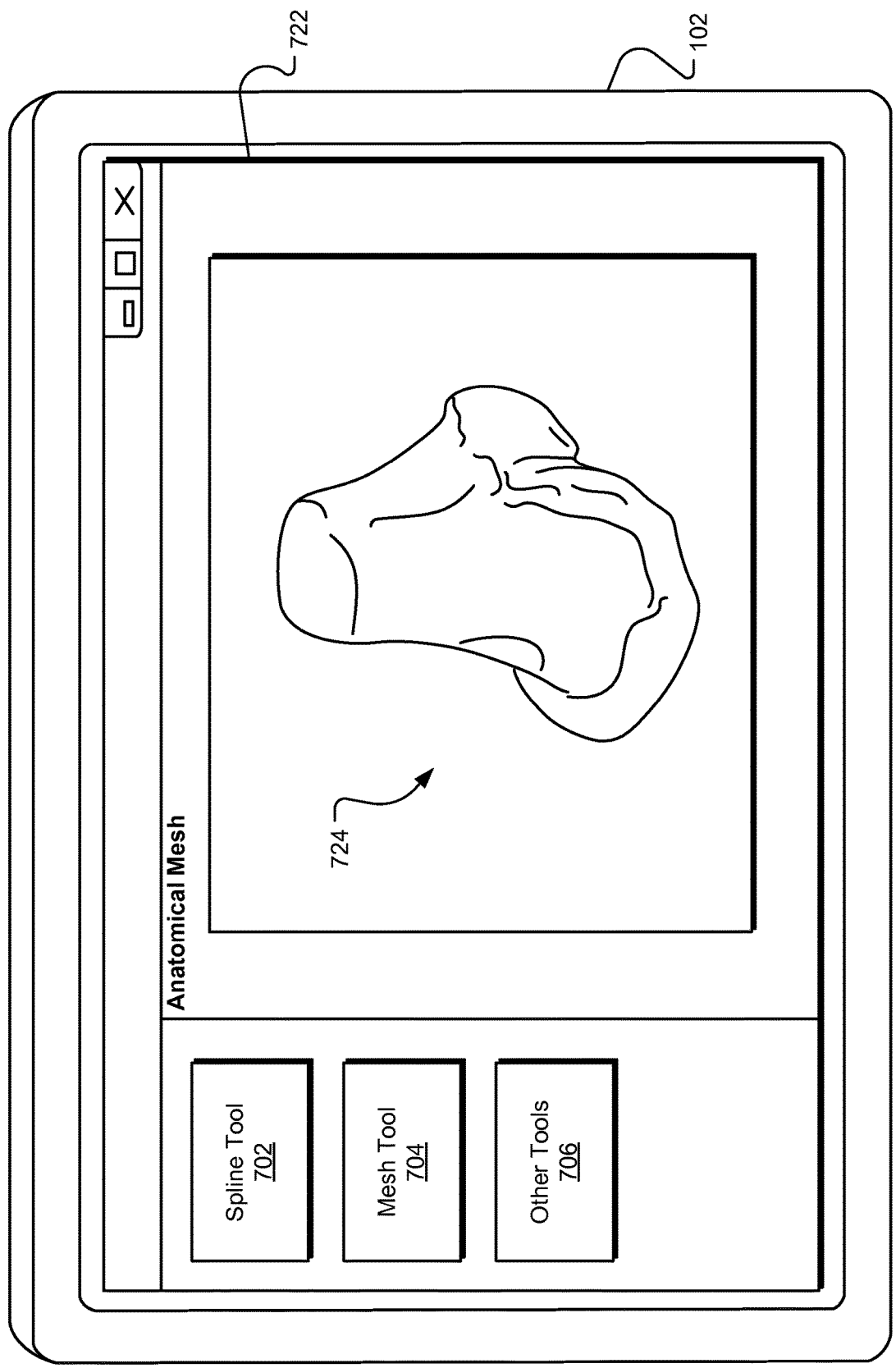
FIG. 15 shows the user interface displaying an anatomical femur model.

Turning to FIG. 15, an anatomical mesh user interface 722 generated by the processor 104 of the computing device 102 and presented on the display 108 of the computing device is shown. In one implementation, the anatomical mesh user interface 722 is generated using the mesh tool 704 and displays the anatomical femur model 724.

In one implementation, once all the image slices 708 have been segmented as described with respect to FIG. 14, the mesh tool 704 generates the a mesh representing the anatomical femur model 724 using the segmentations. As can be understood from FIG. 15, the anatomical femur model 724 is a 3D model representing the knee region of the patient's femur 710 in its present deteriorated state and includes the outer cortical bone surface 712 and the outer cartilage surface 716 of the distal femur 710. The anatomical femur model 724 further includes whole or partially trimmed osteophytes around the edges of the femoral condyles.

Figure 16:
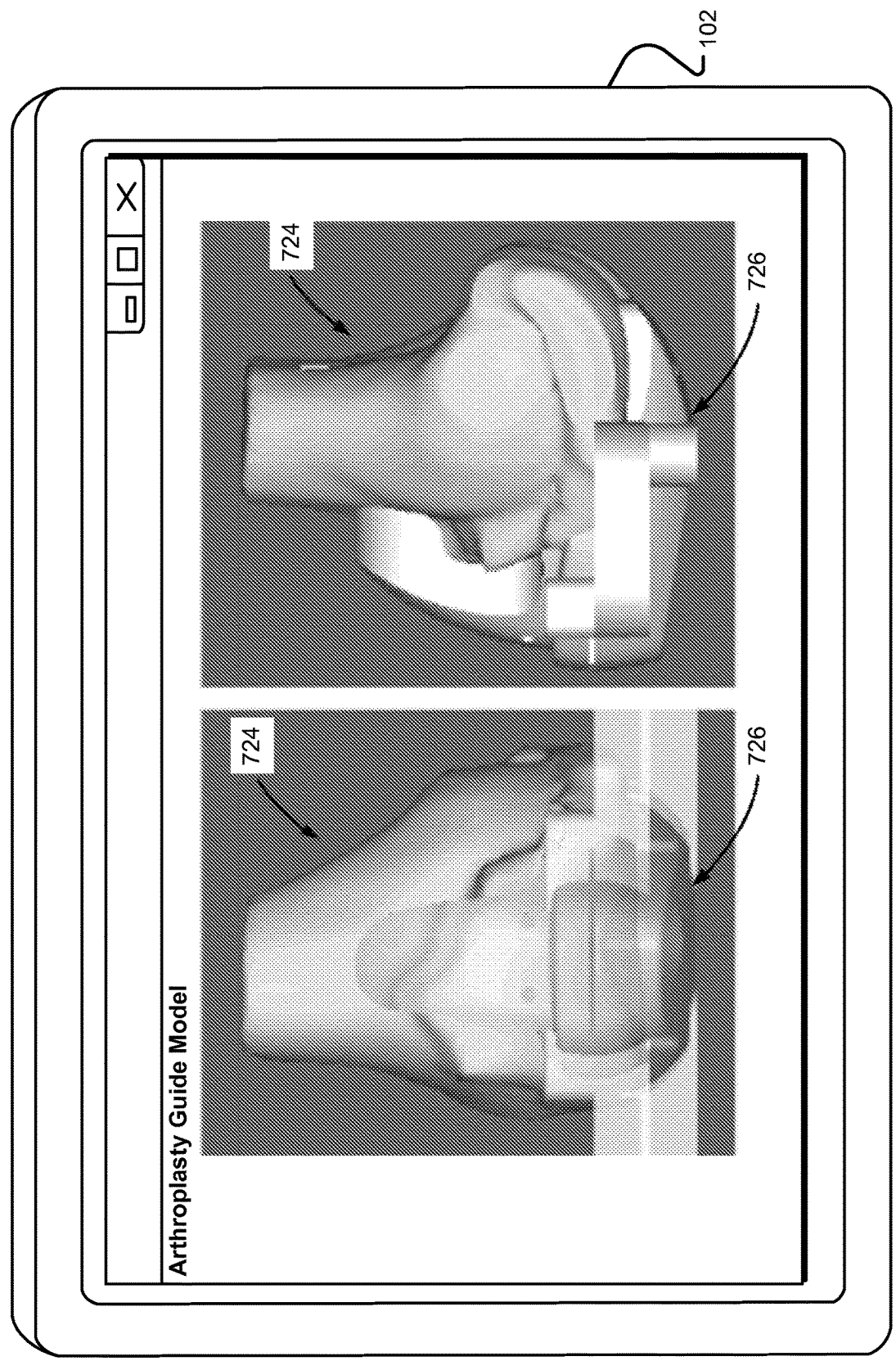
FIG. 16 shows the user interface displaying coronal and sagittal views, respectively, of a three-dimensional arthroplasty guide model superimposed on the anatomical femur model of FIG. 15.

Referring to FIG. 16, coronal and sagittal views, respectively, of a 3D arthroplasty guide model 726 superimposed on the anatomical femur model 724 are shown. As described herein, for example, with respect to FIGS. 9A and 9B, in one implementation, the customized arthroplasty femur jig 400 includes a mating surface 402 that has a surface contour that is generally a surface negative of the corresponding surface of the anterior, distal, and distal-posterior areas of the patient's actual distal femur bone 710. The customized arthroplasty femur jig 400 also includes the resection slot 406 or other planar surface configured to facilitate a distal resection of the patient's distal femur 710 when the mating surface 402 matingly receives the corresponding surface of the actual patient's femur bone 710.

As can be understood from FIG. 16, once the preoperative planning and arthroplasty guide design is completed as described with respect to FIGS. 19-30, the superimposed models 724 and 726 may be output for review, approval, and/or modification by a surgeon. Because the anatomical femur model 724 accurately depicts the patient's distal demur region complete with cartilage and osteophytes in its current deteriorated state, the proposed arthroplasty guide design represented by the arthroplasty guide model 726 has increased accuracy. The surgeon may use the arthroplasty guide model 726 superimposed on the anatomical femur model 724 in the Operating Room to visually confirm that application of the customized arthroplasty femur jig 400 onto the patient bone matches the guide positioning determined during preoperative planning.

Figure 17:
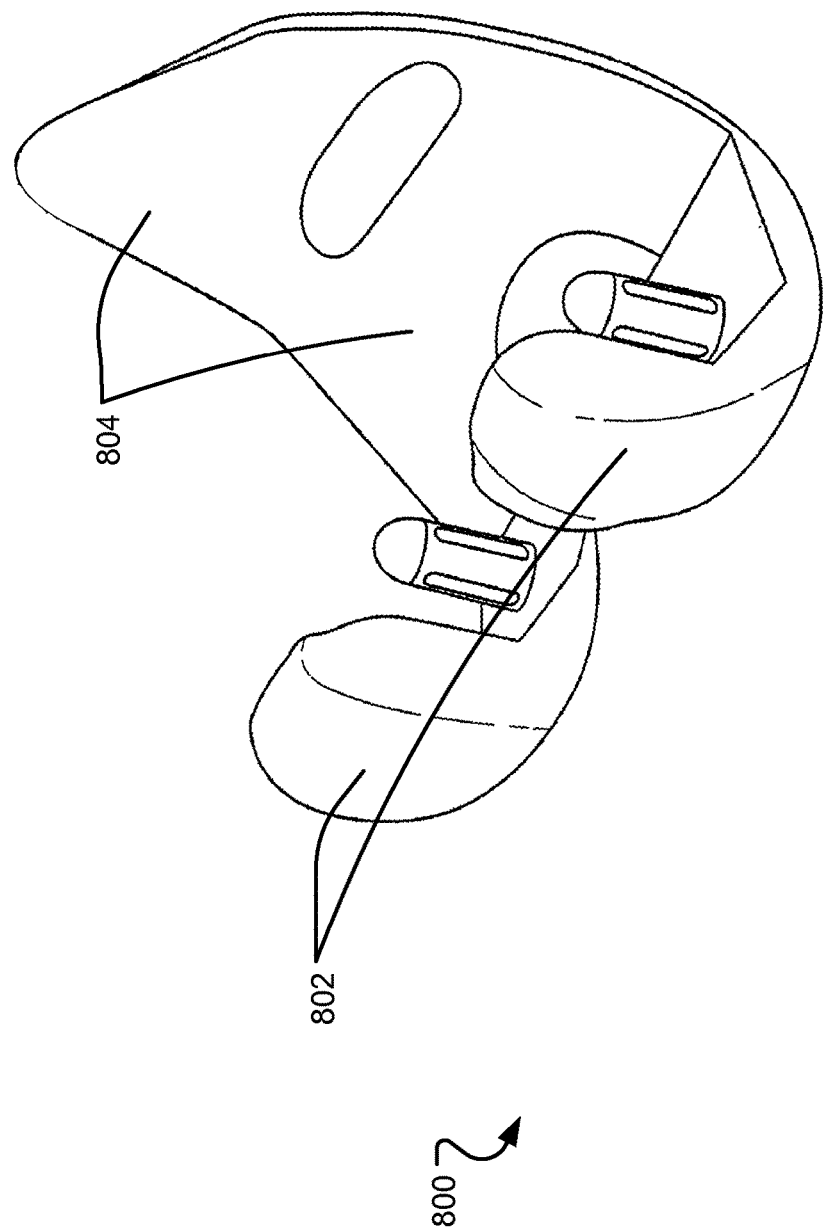
FIG. 17 is a side isometric view of a femoral arthroplasty implant.

FIG. 17 is a side isometric view of a femoral arthroplasty implant 800. In one implementation, the implant 800 includes smooth articular condyle surfaces 802 and an interior bone contacting surface 804 configured to abut against the resected surfaces of the patient's distal femur.

Figure 18:
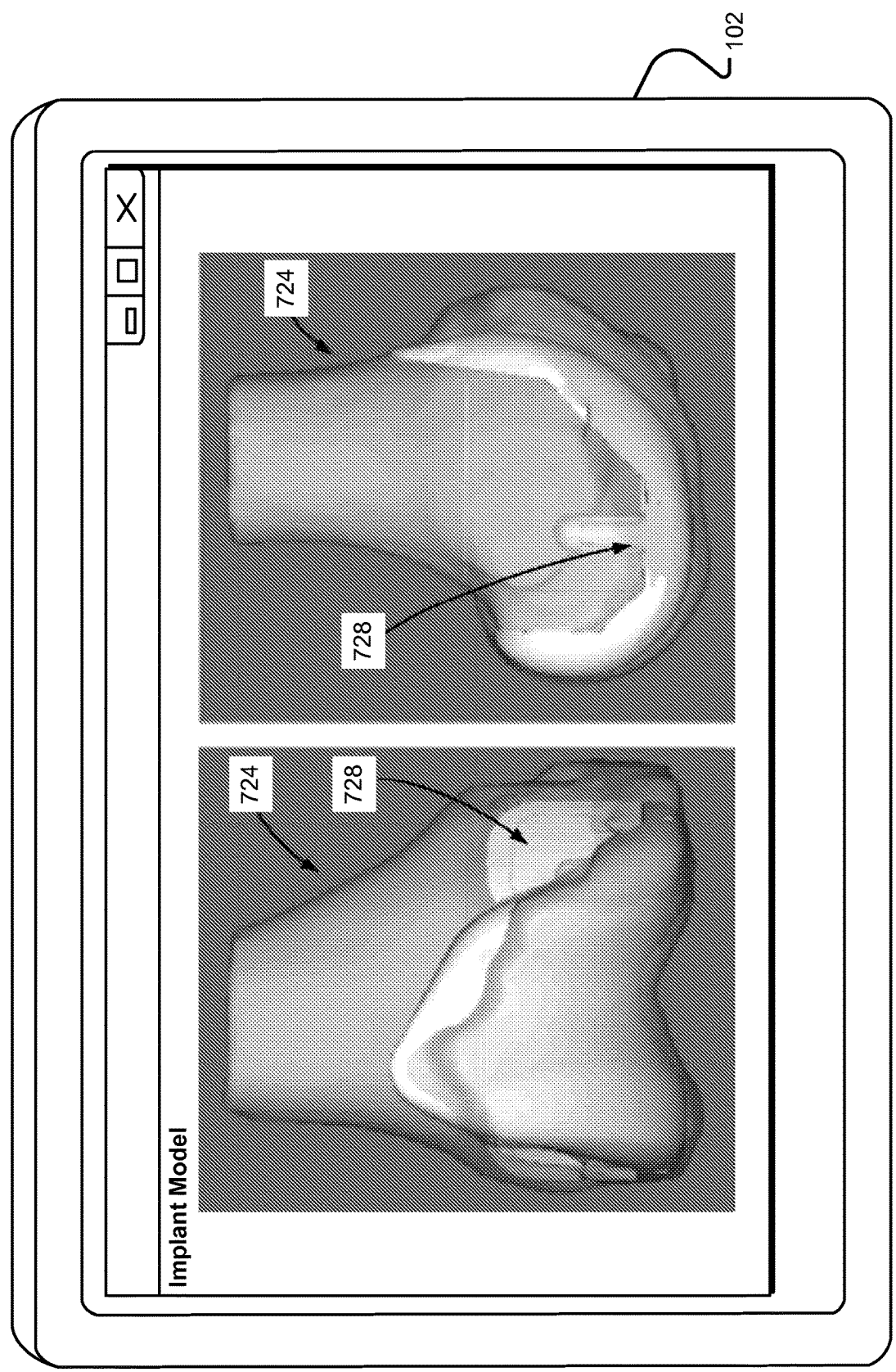
FIG. 18 shows the user interface displaying coronal and sagittal views, respectively, of a three-dimensional implant model superimposed on the anatomical femur model of FIG. 15.

Referring to FIG. 18, coronal and sagittal views, respectively, of a 3D implant model 728 superimposed on the anatomical femur model 724 are shown. In one implementation, once the preoperative planning and arthroplasty guide design is completed as described with respect to FIGS. 19-30, the superimposed models 724 and 728 may be output for review, approval, and/or modification by a surgeon. Because the anatomical femur model 724 accurately depicts the patient's distal demur region complete with cartilage and osteophytes in its current deteriorated state, the proposed implant location and orientation represented by the superimposed models 724 and 728 has increased accuracy.

Figure 19:
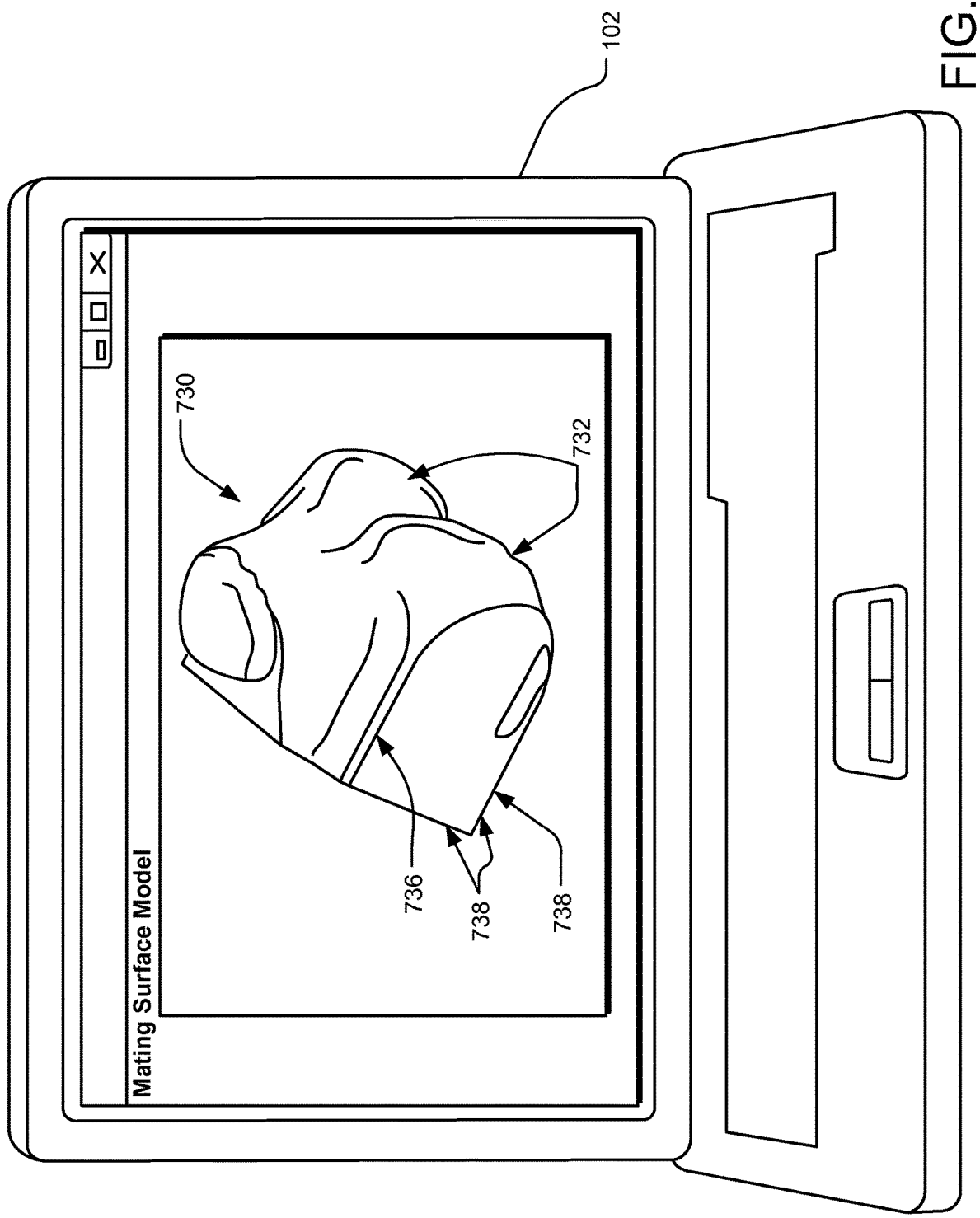
FIG. 19 shows the user interface displaying a medial-anterior isometric view of a mating surface model.

Once the anatomical femur model 724 is generated as described with respect to FIGS. 14-18, the mating surface model 730 is generated. FIG. 19 shows a medial-anterior isometric view of the mating surface model 730. The mating surface model 730 is used to define the mating surface 402 and the resection slot 406 in the customized arthroplasty femur jig 400. The generation of the customized arthroplasty femur jig 400, including he mating surface 402 and the resection slot 406, based on the mating surface model 730 may be similar to the systems and methods disclosed in U.S. patent application Ser. No. 12/546,545, entitled "Arthroplasty System and Related Methods" and filed August 24, and in U.S. patent application Ser. No. 11/959,344, entitled "System and Method for Manufacturing Arthroplasty Jigs" and filed Dec. 18, 2007, which are both incorporated by reference in their entirety herein.

Figure 20:
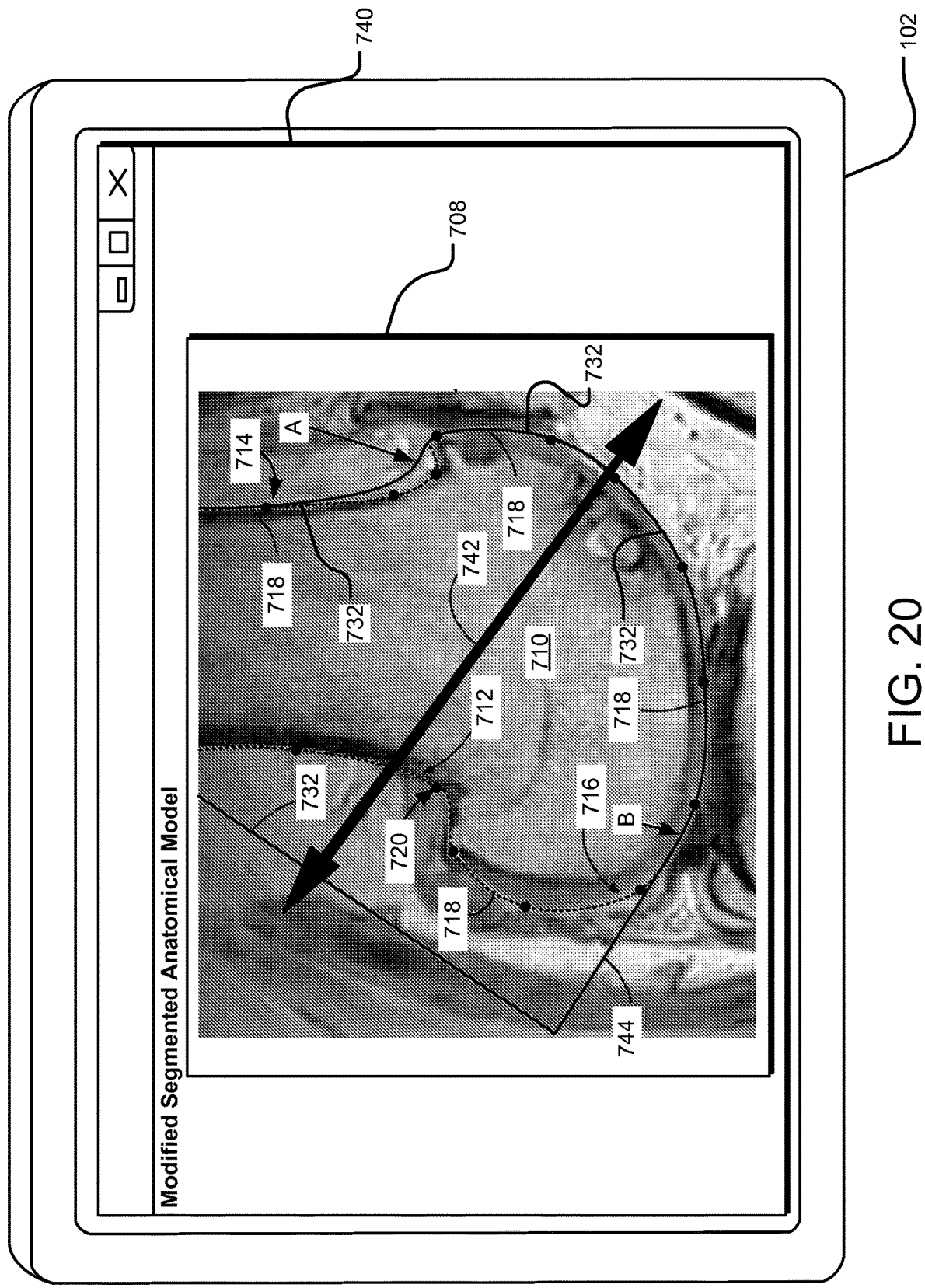
FIG. 20 shows the user interface displaying a sagittal image slice of the patient's femur, wherein the image slice has first been segmented along the actual bone surface (cortical bone and cartilage) followed by modification of the segmentation.

To begin a detailed discussion regarding the generating of the mating surface model 730, reference is made to FIG. 20, which shows a modified segmented anatomical model user interface 740 generated by the processor 104 of the computing device 102 and shown on a display 108 of the computing device 102.

In one implementation, the modified segmented anatomical model user interface 740 displays a sagittal image slice 708 of the patient's femur 710. As can be understood from FIG. 20, the image slice 708 has first been segmented along the actual bone surface (cortical bone and cartilage) followed by modification of the segmentation. The image slice 708 is in an area of the distal femur 710 in the region of the femoral condylar surfaces. In one implementation, after the image slice 708 has been segmented along the actual bone surface as described herein, a push-pull clearance is defined with respect to the femur 710 and depicted in the image slice 708. Stated differently, a push-pull direction 742 corresponds to a line of action along which the customized arthroplasty femur jig 400 will approach and withdraw from an anterior-distal region of the articular region of the patient's actual distal femur during the arthroplasty procedure.

As indicated at arrow B in FIG. 20, in one implementation, the push pull direction 724 is applied as a tangent 744 to the articular condylar region of the segmenting spline 718 segmenting the outer cartilage surface 716 of the femur condylar region. Stated differently, in one implementation, the push-pull direction 742 is applied as a tangent 744 to the segmenting spline 718, segmenting the outer cartilage surface 716 of the femur condylar region. The point of tangential contact between the tangent 744 and the articular region of the segmenting spline 718 indicates a point in the posterior direction past which the mating region of the customized arthroplasty femur jig 400 will not contact any point of the bone surface or volume shaded by the tangent line, defining a non-reachable area of the bone surface. Similarly, the contour is modified at any other point on the segmenting spline 718 that is tangent to the push-pull direction 742 to circumscribe the non-reachable area. An example of this is shown in region A of FIG. 20. As can be understood from FIG. 20, the tangent 744 forms part of a modified closed contour 732 (shown in solid lines). In one implementation, the modified closed contour 732 extends along the segmenting spline 718 along most anterior and distal areas of the distal femur 710 but is substantially offset from the segmenting spline 718 along the posterior regions and posterior-distal regions of the femur 710.

Figure 21:
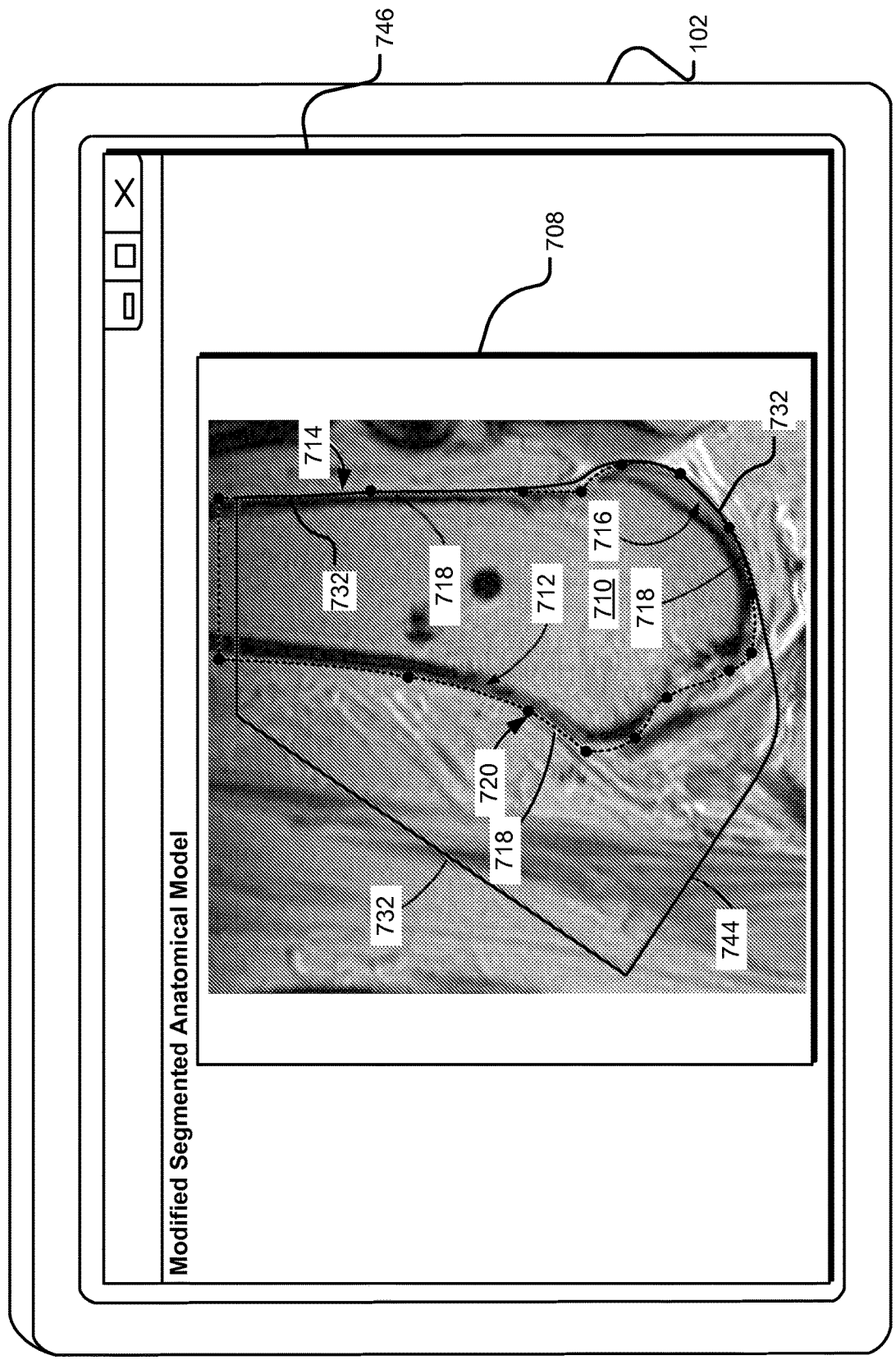
FIG. 21 illustrates the user interface displaying another sagittal image slice of the patient's femur, wherein the image slice has first been segmented along the actual bone surface followed by modification of the segmentation.

Referring to FIG. 21, another modified segmented anatomical model user interface 746 generated by the processor 104 of the computing device 102 and shown on a display 108 of the computing device 102.

In one implementation, the modified segmented anatomical model user interface 746 displays another sagittal image slice 708 of the patient's femur 710. As shown in FIG. 21, the image slice 708 has first been segmented along the actual bone surface, as described herein, followed by modification of the segmentation.

Unlike the image slice 708 shown in FIG. 2, the image slice 708 shown in FIG. 21 is of a trochlear groove region of the distal femur 710. Further, unlike the image slice 708 of FIG. 20, the tangent 744 of FIG. 21 does not come close to the segmenting spline 718. Instead, the tangent 744 is offset by a specified amount, which is a parameter for modifying the segmentation. The offset of the tangent 744 compensates for poorly defined cartilage and soft tissue boundaries in the image slice 708. In one implementation, the offset is approximately 1-10 mm. However, other specified values are contemplated. The span of slices 708 over which the offset is applied comprises an offset region.

In one implementation, the offset region is defined beginning at the medial and lateral edges of the condylar surfaces of the distal femur 710 and moving inward to the trochlear groove of the distal femur 710 to meet at the medial-lateral center of the trochlear groove. Applying the tangent 744 along with respective offsets to create the closed modified contour 732 results in the overestimated 3D mating surface model 730 shown in FIG. 19.

Stated differently, as can be understood from FIGS. 19 and 21, the mating surface model 730 includes surfaces 732 that accurately replicate the corresponding condylar surfaces of the patient's femur 710 in those areas of the image slices 708 that can result in accurate model surfaces and those areas of the patient's femoral condylar surfaces that can be accurately manufactured into the mating surface 402 of the customized arthroplasty femur jig 400.

In one implementation, the mating surface model 730 also includes overestimated surfaces 734 resulting from the corresponding splines 718 being moved outwardly for those surfaces of the patient's femur 710 corresponding to those areas of the image slices 708 that are likely inaccurate due to imaging limitations, are unlikely to be manufactured accurately due to manufacturing limitations, or are excluded due to mechanical or surgical constraints of applying the customized arthroplasty femur jig 400 to the bone. The overestimated surfaces 734 may further include tangential overestimated surfaces 738 corresponding to the tangent 744.

Figure 22:
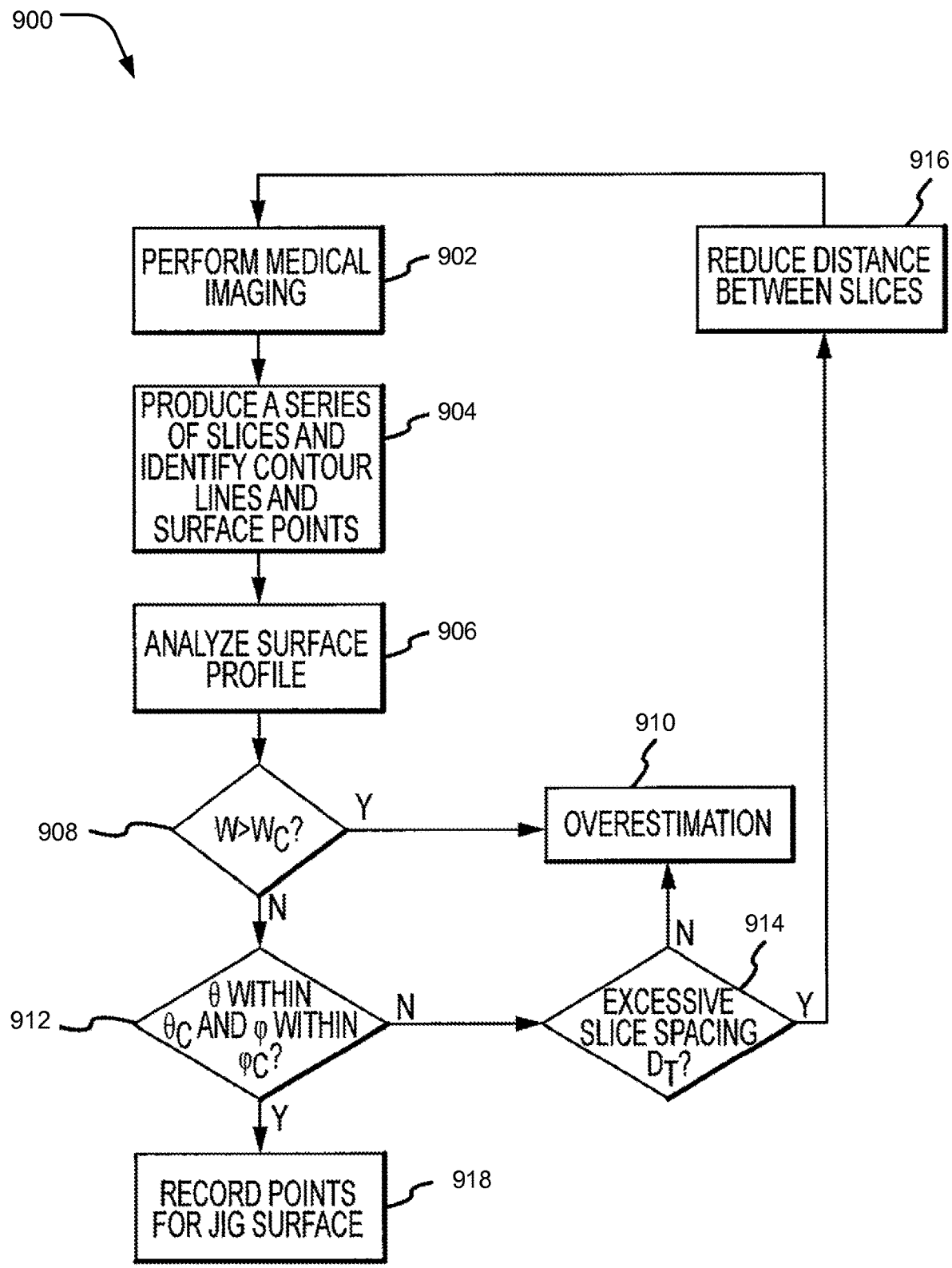
FIG. 22 illustrates example operations for identifying and adjusting irregular contour line regions using overestimation.

For a detailed discussion of example operations 900 for identifying and adjusting irregular contour line regions using overestimation, reference is made to FIG. 22. In one implementation, the operations 900 represent an example overestimation algorithm that may be used to identify and adjust for irregular regions when forming the mating surface model 730. A performing operation 902 performs medical imaging on the damaged bone at desired slice thicknesses, $D_T$. For example, MRI and/or CT scans may be performed at predetermined thicknesses. In some embodiments, the desired thickness is set at 2 mm or any other thickness.

From this medical imaging, a producing operation 904 produces a series of the image slices 708 and uses image segmentation processes to generate the contour lines. In one implementation, the producing operation 904 identifies a plurality of surface coordinate points along each contour line segment with respect to contour line. For example, the points in the irregular region corresponding to contour line segment may be identified and indexed as i-n, . . . , i−1, i, i+1, i+2, i+3, . . . , i+n.

With the surface coordinate points along the contour defined, an analyzing operation 906 analyzes two or more of the points (e.g., i and i+1) to determine if an irregularity exists in the contour line segment. In some implementations, the analyzing operation 906 may be performed repetitively on each point within the contour segment.

In one implementation, the analyzing operation 906 may include constructing one or more tangent lines corresponding to the points in the irregular region. An operation 908 calculates differences between the angles formed by one or more of the tangent lines. In one implementation, the angular difference $w_i$ may indicate whether portions of the contour line segment are too eccentric for use in constructing the mating surface model 730. The operation 908 compares the angular difference $w_i$ to a predetermined angular criterion $w_c$. The angular criterion $w_c$ may be determined based on several factors, including the physical dimensions and characteristics of the machining system 110. In some implementations, the predetermined angular criterion $w_c$ is set at approximately 5 degrees. In other implementations, the predetermined angular criterion $w_c$ is set at between approximately 5 degrees and approximately 20 degrees. If the comparison by the operation 908 indicates that the angular difference $w_i$ is greater than the predetermined criterion $w_c$, then an overestimating operation 910 modifies the data associated with the irregular contour line segment by overestimating (e.g., adjusting the irregular contour line segment outward or away from the bone portion of the image slice 718).

If the angular differences associated with a contour line of a particular slice 708 fall within the angular criterion $w_c$, and the points are used as a potential jig surface, then surface variation between contour lines of adjacent slices may be checked in an operation 912. This approach may help to identify certain areas where no cartilage damage or osteophyte is observed in the imaging, yet there is a need to overestimate because the surface variation, between the adjacent slices 708, may be too great to be used as an accurate representation of the actual bone surface to be a potential femoral jig surface. Example areas falling within this category for the femoral condyle include, without limitation, the area of anterior condylar portion close to the trochlear groove and the area of distal condylar portion close to the intercondylar notch to name a few examples.

In one implementation, as reflected in an operation 914, when one or more coordinate points fail to meet both the criterion of the operations 908 and 912, a determination may be made regarding whether or not the slice thickness $D_T$ may be adjusted to a thinner slice thickness. Reducing the slice thickness $D_T$ per the operation 914 may reduce the variations between adjacent contour lines, making it more likely that the operations 908 and 912 will be satisfied for the coordinate points were the entire process started over at the performing operation 902 with a new slice thickness $D_T$. If it is determined that modifying the slice thickness $D_T$ would not be beneficial (e.g., due to slice thickness $D_T$ already being at a minimum because further reduction in slice thickness $D_T$ may generate significant high interferences, residuals, signal-to-noise ratios and unreliable volume-averaging in the pixels), then the overestimating operation 910 may subject the contour lines to overestimation.

If the one or more coordinate points of a contour line satisfy the tangent angle criterion of the operation 908 and both of the angular criterion of the operation 912, then a recording operation 918 records the one or more coordinate points for the generation of the jig's bone mating surface. In other words, if the one or more coordinate points of a contour line satisfy the tangent angle criterion the operation 908 and both of the angular criterion of the operation 912, then the surfaces associated with such one or more coordinate points may be employed in the generation of corresponding bone mating surfaces of the jig.

For a further detailed discussion of overestimation in the context of femoral models and those areas likely to replicate accurately with respect to both imaging and manufacturing, reference is made to U.S. patent application Ser. No. 12/505,056, entitled "System and Method for Manufacturing Arthroplasty Jigs having Improved Mating Accuracy" and filed Jul. 17, 2009. The identification of the splines 718 that should be overestimated and methods of overestimating such segments may be similar to the systems and methods disclosed in U.S. patent application Ser. No. 12/505,056.

Figure 23:
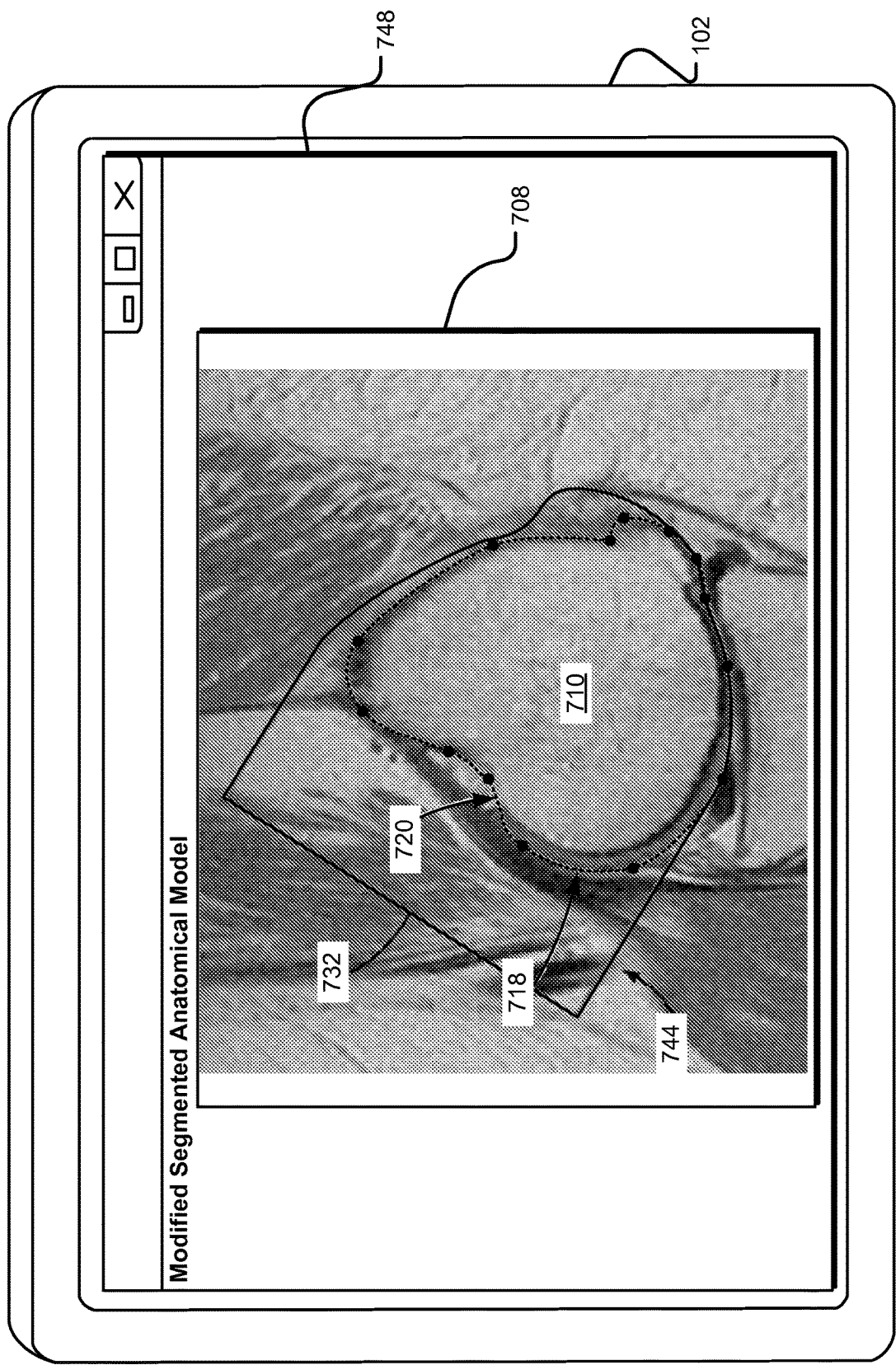
FIG. 23 shows the user interface displaying a sagittal image slice of the patient's femur, wherein the image slice has been provided with both a spline and a modified contour with the image slice being near an extreme medial or lateral side of the patient's femur.

Turning to FIG. 23, another modified segmented anatomical model user interface 748 generated by the processor 104 of the computing device 102 and shown on a display 108 of the computing device 102 is illustrated.

In one implementation, the modified segmented anatomical model user interface 748 displays another sagittal image slice 708 of the patient's femur 710. As can be understood from FIG. 23, the image slice 708 has been provided with both the segmenting spline 718 and the modified contour 732 with the image slice 708 being near an extreme medial or lateral side of the patient's femur 710. In one implementation, as can be understood from the segmenting spline 718 of FIG. 23, since the image slice 708 of FIG. 23 is so extreme medial or lateral and because of potential presence of osteophytes, which are difficult to image, along these areas of the bone, the mating surface 402 of the customized arthroplasty femur jig 400 will not make contact with the femur 710 in this location. Accordingly, overestimation is applied to each successively more medial or lateral outwardly located image slice 708, resulting in the medial and lateral cylindrical extensions 736 shown in FIG. 19.

Figure 24:
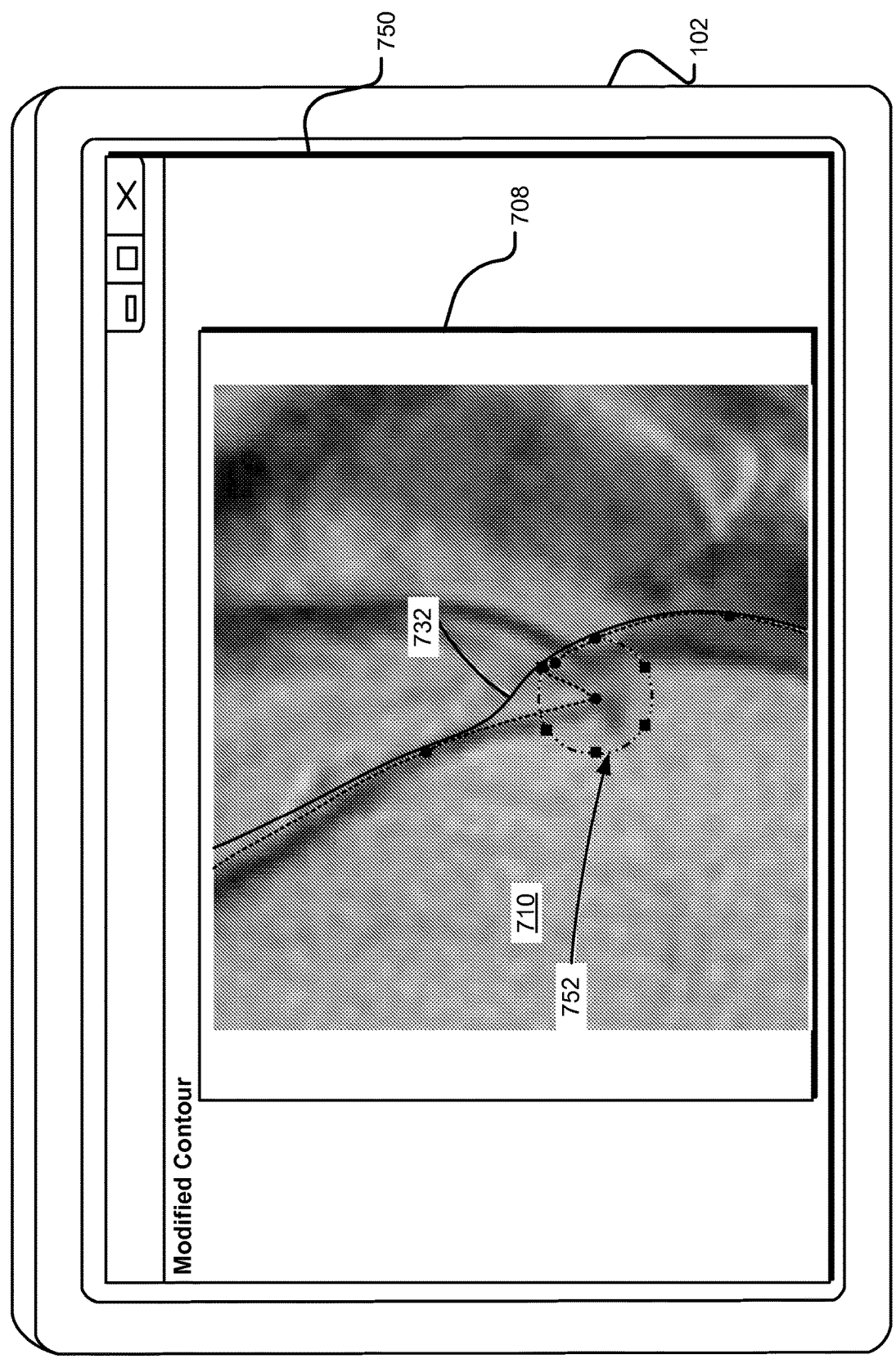
FIG. 24 shows the user interface displaying an enlarged view of a portion of a modified contour, wherein a minimum radius circle is depicted in a region of the surface of the femur, such that if it could not be inscribed inside the mating surface contour, the resulting surface feature would be too small to be replicated during manufacturing.

FIG. 24 shows a modified contour user interface 750 generated by the processor 104 of the computing device 102 and shown on a display 108 of the computing device 102 is illustrated.

In one implementation, the modified contour user interface 750 displays an enlarged view of a portion of a modified mating surface contour 732, wherein a minimum radius circle 752 is depicted in a region of the surface of the femur 710, such that if it could not be inscribed inside the modified mating surface contour 732, the resulting surface feature would be too small to be replicated during manufacturing. Accordingly, the modified mating surface contour 732 is bumped outwardly (i.e., overestimated) to increase the radius of curvature in the area indicated by the minimum radius circle 752. In one implementation, the curvature of the radius associated with the minimum radius circle 752 is greater than 3.5 mm, such that the modified mating surface contour 732 does not have a radius that is less than 3.5 mm. This minimal-curvature adjustment is iteratively applied along all points on the mating surface model 730 within the slices 708, as well as between slices in all cross-sections.

Figure 25:
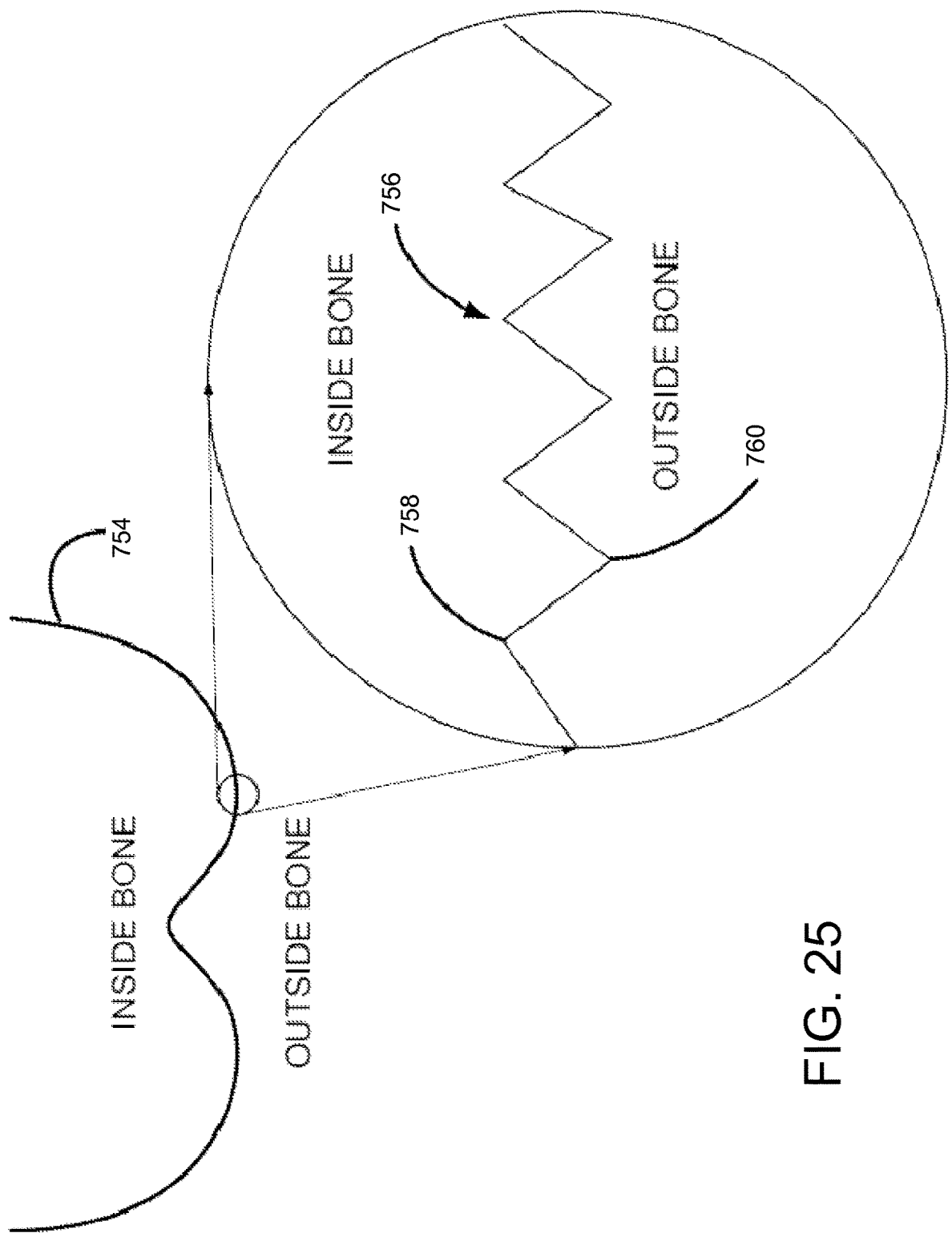
FIG. 25 illustrates a substantially magnified segment of a modified surface.

For a detailed discussion of smoothing a modified mating surface 754, reference is made to FIG. 25, which illustrates a schematic coronal cross-section of the segmented distal femoral surface, along with a substantially magnified sub-region of that surface. Since FIG. 25 is a coronal view of a surface defined by the modified mating surface contours 732 that were created in sagittal slices 708, it shows where the modified mating surface contours 732 intersect the coronal plane.

As shown in FIG. 25, the intersection points of the modified mating surface contours 732 with the coronal plane may not form a curve 756 that is smooth. Instead, the curve 756 may feature one or more peaks 758 and valleys 760. In one implementation, the sub-region of the coronal cross-section curve 756 is smoothed along with the rest of the segments of the cross-section 754, without causing the modified mating surface contours 732 to underestimate (i.e., encroach into the "Inside Bone" region of the image slice 708 shown in FIG. 25). Instead, the sub-region of the coronal cross-section curve 756 is smoothed, along with the rest of the cross-section 754 to overestimate (i.e., extend into the "Outside Bone" region of the image slice 708 shown in FIG. 25). It will be appreciated that the "Inside" to "Outside" direction vector may vary depending on the region of the bone surface and is generally orthogonal to the bone surface.

Figure 26:
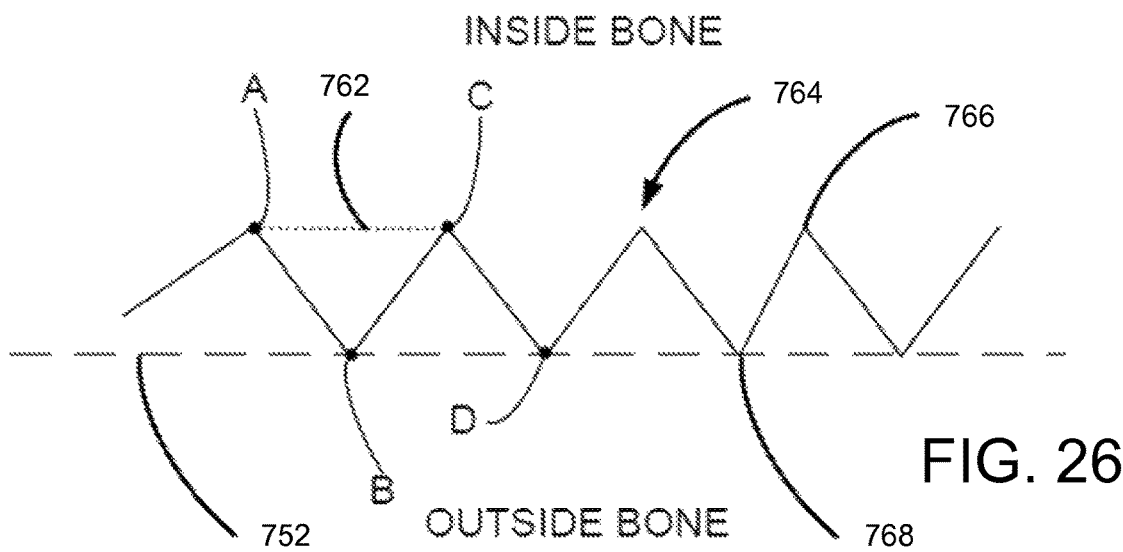
FIGS. 26-28 depict the surface of FIG. 25 at different stages of smoothing the surface segments without underestimating.
Figure 27:
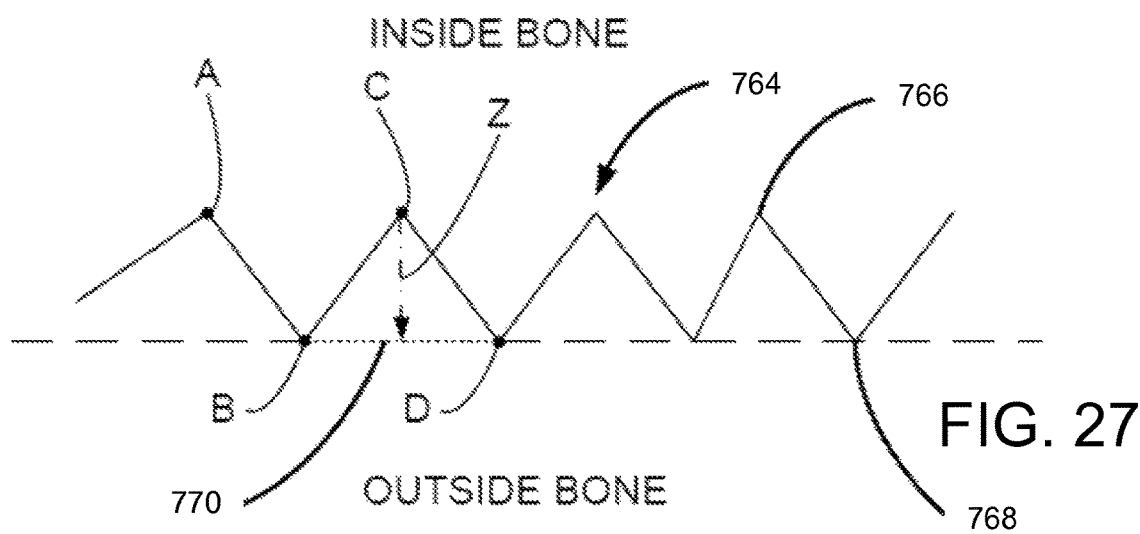
Figure 28:
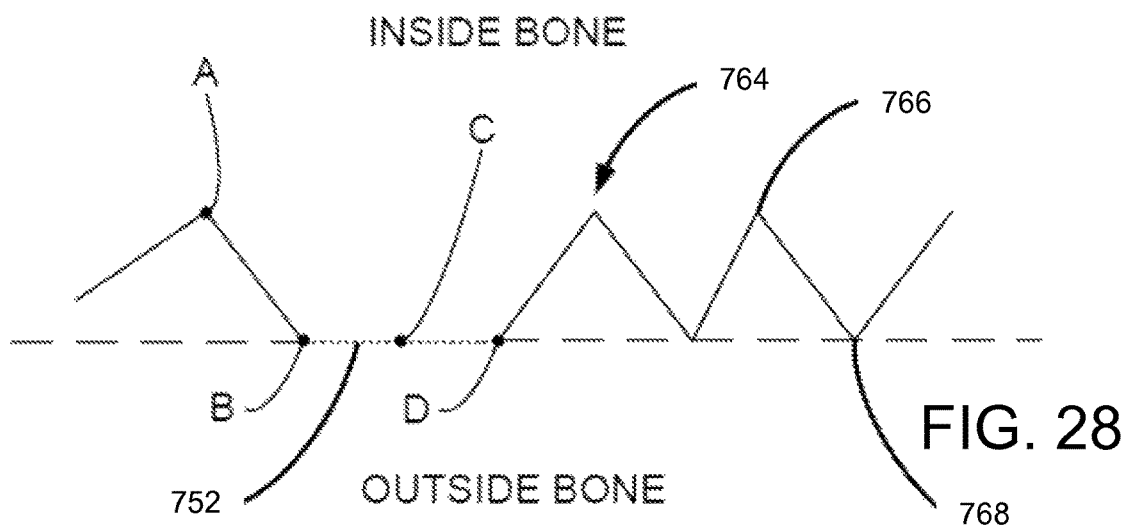

FIGS. 26-28 depict the sub-region of the coronal cross-section curve 756 of FIG. 25 at different stages of smoothing the cross-section 754 without underestimating. In one implementation, the minimum radius circle 752 shown in FIG. 26 as a dashed line illustrates the most outward extent of the coronal cross-section peaks 758. A first line segment 762 is extended across a first set of three points A-C, thereby determining if the middle point B lies inward or outward of the first line segment 762. If the middle point B is inward of the first line segment 762, then the middle point B is moved to reside on the first line segment 762. Conversely, if the middle point B is on or outward of the first line segment 762, as shown in FIG. 26, then the middle point B stays in place.

As shown in FIG. 27, a second line segment 770 is extended across a second set of three points B-D, thereby determining if the middle point C is inward of or on the second line segment 770. If the middle point C is inward of the second line segment 770, as shown in FIG. 27, then the middle point C is moved to reside on the second line segment 770 as indicated by the arrow Z in FIG. 27 and as shown in FIG. 28. Conversely, if the middle point C is on or outward of the second line segment 770, then the middle point C stays in place similar to the middle point B of FIG. 26. This process is repeated along the entire perimeter of each coronal cross-section 754 until the coronal cross-section 754 is fully smoothed. In one implementation, in addition to smoothing coronal cross-sections 754, the mating surface model 730 cross-sections are similar smoothed in every cross-section using the process as described with respect to FIGS. 25-28.

Figure 29:
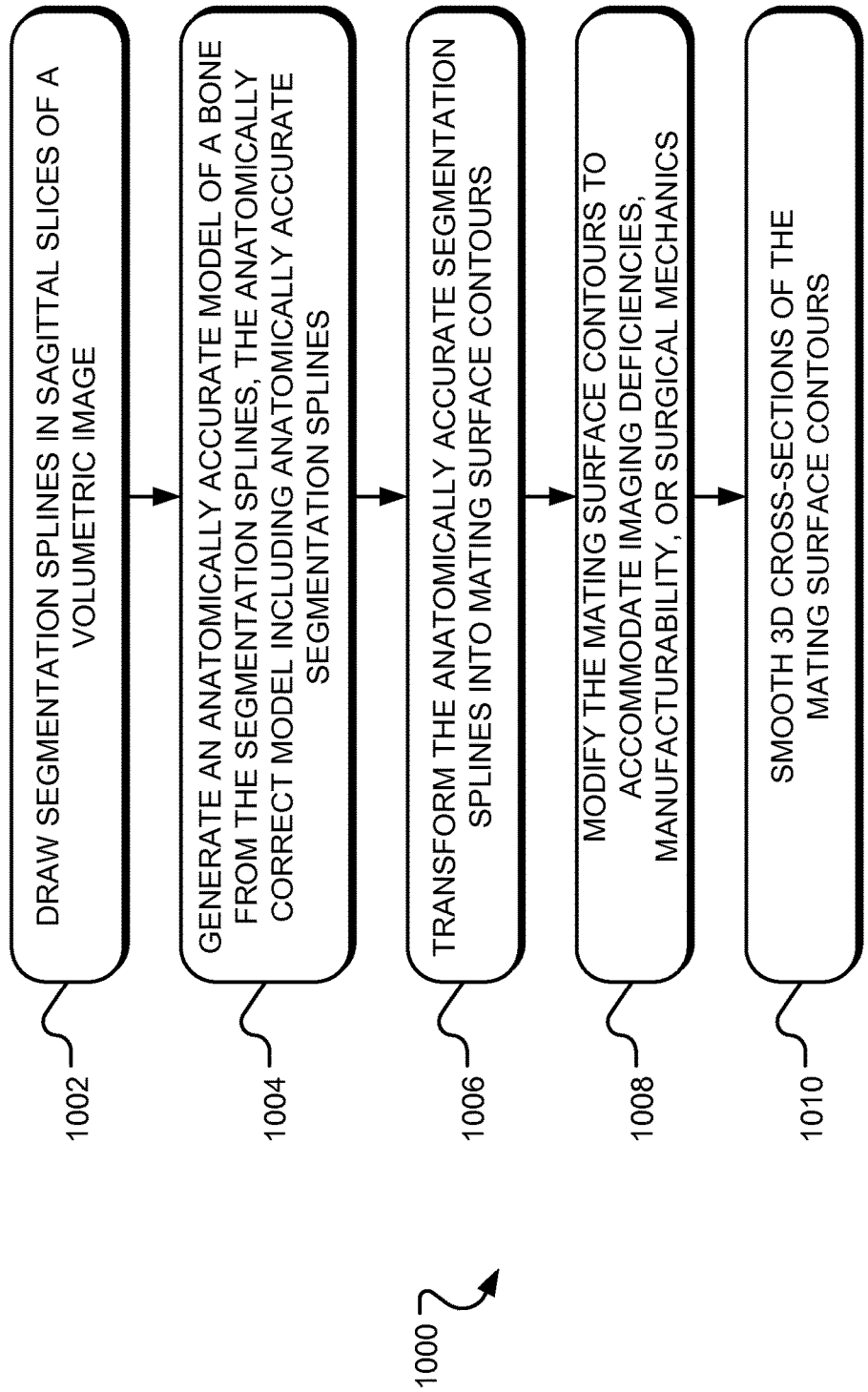
FIG. 29 illustrates example operations for generating a smooth mating surface model.

FIG. 29 illustrates example operations 1000 for generating a smooth mating surface model. In one implementation, the operations 1000 smooth a mating surface model, extending along at least one of a bone, cartilage, or osteophyte surface model in a medical image of a patient bone. The operations 1000 incorporate various adjustments and overestimations to compensate for constraints in imaging, manufacturability, and surgical application, as described herein.

In one implementation, a drawing operation 1002 draws segmentation splines in sagittal slices of a volumetric image. A generating operation 1004 generates an anatomically accurate model of a bone from the segmentation splines. The anatomically accurate model includes anatomically accurate segmentation splines. A transforming operation 1006 transforms the anatomically accurate segmentation splines into mating surface contours. A modifying operation 1008 modifies the mating surface contours to accommodate imaging deficiencies, manufacturability, and/or surgical mechanics. A smoothing operation 1010 smooths 3D cross-sections of the mating surface contours. Once the mating surface contours are smoothed, the smoothed mating surface contours may be used to generated a mating surface model. The mating surface model may be used during preoperative planning and to generate manufacturing instructions for a customized arthroplasty jig. In one implementation, the manufacturing instructions are output to a machining system, such as a CNC machine or SLA machine, which is configured to manufacture the customized arthroplasty jig.

Figure 30:
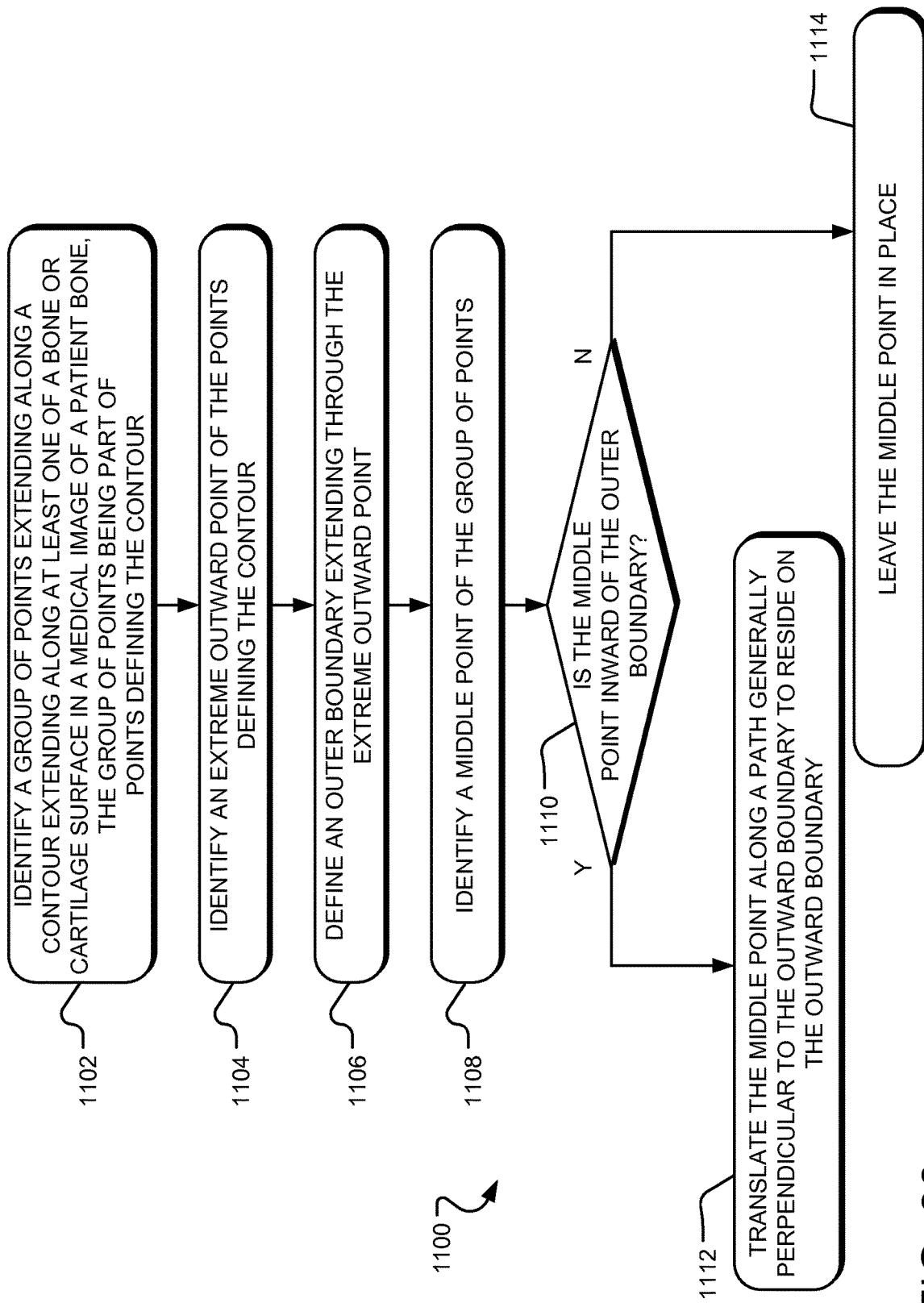
FIG. 30 illustrates example operations for smoothing a contour extending along at least one of a bone or cartilage surface in a medical image of a patient bone.

FIG. 30 illustrates example operations 1100 for smoothing a contour extending along at least one of a bone or cartilage surface in a medical image of a patient bone. The smoothing operation 1010 of FIG. 29 may comprise the operations 1100.

In one implementation, an identifying operation 1102 identifies a group of points extending along a modified mating surface contour. The modified mating surface contour extends along at least one of a bone or cartilage surface in a medical image of a patient bone. The group of points are part of points defining the modified mating surface contour. Another identifying operation 1104 identifies an extreme outward point of the points defining the modified mating surface contour. A defining operation defines an outer boundary extending through the extreme outward point. An identifying operation 1108 identifies a middle point of the group of points. An operation 1110 determines whether the middle point is inward of the outer boundary. If the middle point is inward of the outer boundary, a translating operation 1112 translates the middle point along a path generally perpendicular to the outward boundary to reside on the outward boundary. If the middle point is outward of the outer boundary, a leaving operation 1114 leaves the middle point in place.

Figure 31:
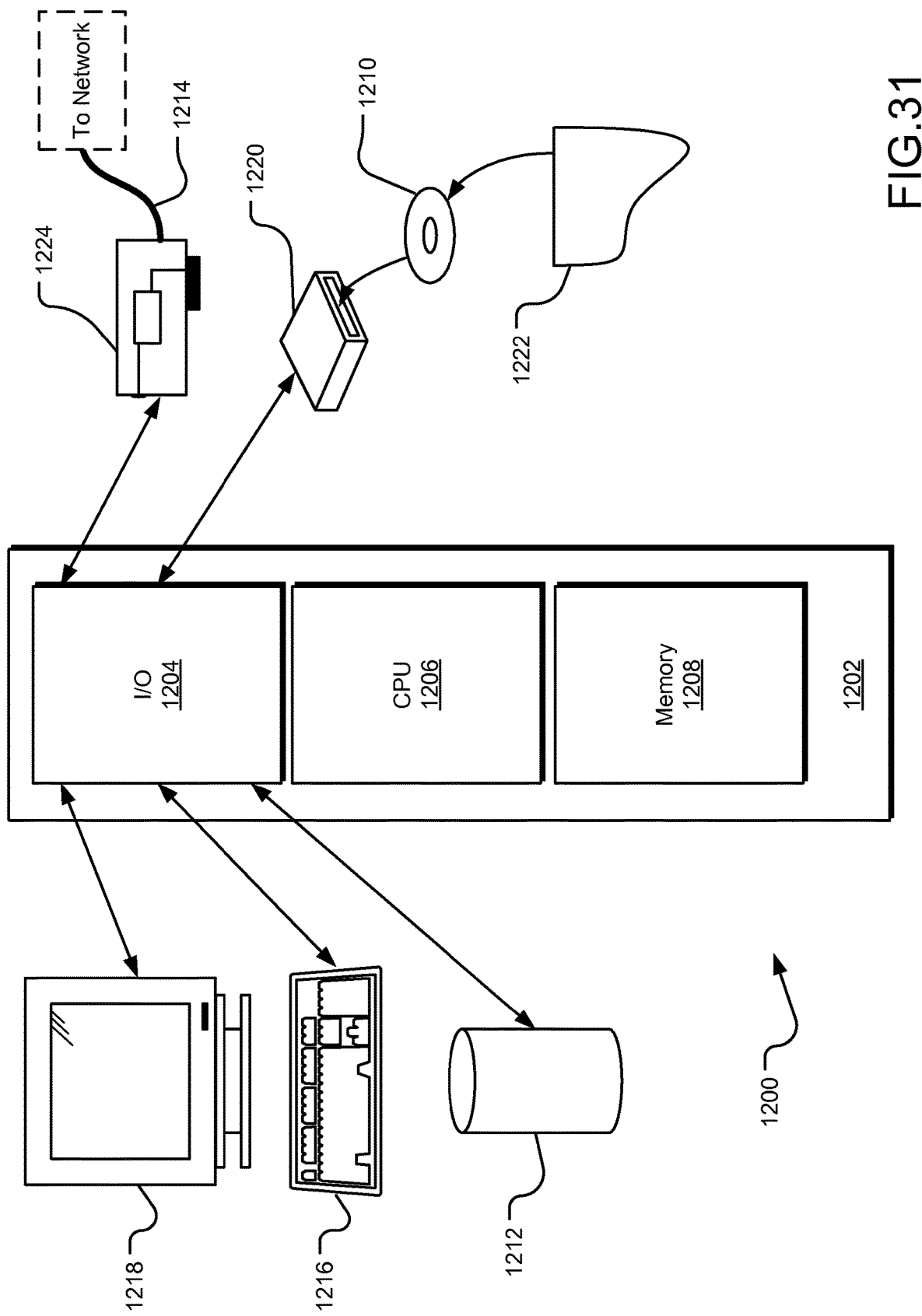
FIG. 31 is an example of a computing system that may implement various systems and methods discussed herein.

FIG. 31 is an example computing system 1200 that may implement various systems and methods discussed herein. A general purpose computer system 1200 is capable of executing a computer program product to execute a computer process. Data and program files may be input to the computer system 1200, which reads the files and executes the programs therein. Some of the elements of a general purpose computer system 1200 are shown in FIG. 31, wherein a processor 1202 is shown having an input/output (I/O) section 1204, a Central Processing Unit (CPU) 12906, and a memory section 1208. There may be one or more processors 1202, such that the processor 1202 of the computer system 1200 comprises a single central-processing unit 1206, or a plurality of processing units, commonly referred to as a parallel processing environment. The computer system 1200 may be a conventional computer, a distributed computer, or any other type of computer, such as one or more external computers made available via a cloud computing architecture. The presently described technology is optionally implemented in software devices loaded in memory 1208, stored on a configured DVD/CD-ROM 1210 or storage unit 1212, and/or communicated via a wired or wireless network link 1214, thereby transforming the computer system 1200 in FIG. 12 to a special purpose machine for implementing the described operations.

The I/O section 1204 is connected to one or more user-interface devices (e.g., a keyboard 1216 and a display unit 1218), a disc storage unit 1212, and a disc drive unit 1220. Generally, the disc drive unit 1220 is a DVD/CD-ROM drive unit capable of reading the DVD/CD-ROM medium 1210, which typically contains programs and data 1222. Computer program products containing mechanisms to effectuate the systems and methods in accordance with the presently described technology may reside in the memory section 1204, on a disc storage unit 1212, on the DVD/CD-ROM medium 1210 of the computer system 1200, or on external storage devices made available via a cloud computing architecture with such computer program products, including one or more database management products, web server products, application server products, and/or other additional software components. Alternatively, a disc drive unit 1220 may be replaced or supplemented by a floppy drive unit, a tape drive unit, or other storage medium drive unit. The network adapter 1224 is capable of connecting the computer system 1200 to a network via the network link 1214, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 1200 is connected (by wired connection or wirelessly) to a local network through the network interface or adapter 1224, which is one type of communications device. When used in a WAN-networking environment, the computer system 1200 typically includes a modem, a network adapter, or any other type of communications device for establishing communications over the wide area network. In a networked environment, program modules depicted relative to the computer system 1200 or portions thereof, may be stored in a remote memory storage device. It is appreciated that the network connections shown are examples of communications devices for and other means of establishing a communications link between the computers may be used.

In an example implementation, the various models and associated data, a plurality of internal and external databases, source databases, and/or data cache on cloud servers are stored as the memory 1208 or other storage systems, such as the disk storage unit 1212 or the DVD/CD-ROM medium 910, and/or other external storage devices made available and accessible via a cloud computing architecture. Modeling software and other modules and services may be embodied by instructions stored on such storage systems and executed by the processor 1202.

Figure 12:
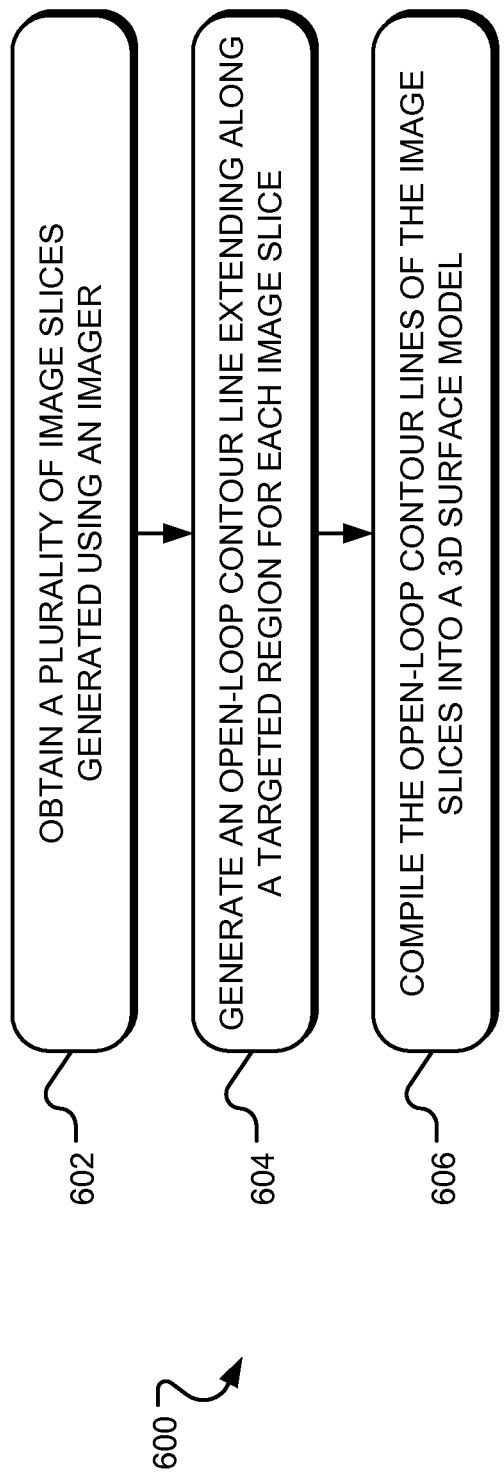
FIG. 12 illustrates example operations for producing a customized femur jig.

Some or all of the operations described herein may be performed by the processor 1202. Further, local computing systems, remote data sources and/or services, and other associated logic represent firmware, hardware, and/or software configured to control operations of the system 100. Such services may be implemented using a general purpose computer and specialized software (such as a server executing service software), a special purpose computing system and specialized software (such as a mobile device or network appliance executing service software), or other computing configurations. In addition, one or more functionalities of the system 100 disclosed herein may be generated by the processor 1202 and a user may interact with a Graphical User Interface (GUI) (e.g., the user interface 120) using one or more user-interface devices (e.g., the keyboard 1216, the display unit 1218, and the computing device 102) with some of the data in use directly coming from online sources and data stores. The system set forth in FIG. 12 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method for generating a smooth mating surface model the method comprising:
    segmenting sagittal slices of a volumetric image of a patient bone with segmentation splines;
    generating an anatomically accurate model of the patient bone from the segmentation splines using at least one processor, the anatomically accurate model including anatomically accurate segmentation splines;
    transforming the anatomically accurate segmentation splines into mating surface contours;
    modifying any inadequate segments of the mating surface contours to obtain modified mating surface contours;
    generating a mating surface model of the patient bone using the at least one processor based on the mating surface contours and the modified mating surface contours; and
    smoothing three-dimensional cross-sections of the mating surface model by removing one or more peaks and valleys in at least one curve of the three-dimensional cross-sections without encroaching into a region corresponding to inside the patient bone to generate the smooth mating surface model, wherein smoothing the three-dimensional cross-sections of the mating surface model comprises:
        identifying a group of points extending along one of the mating surface contours, the group of points being part of points defining the mating surface contour;
        identifying an extreme outward point of the points defining the mating surface contour;
        defining an outer boundary extending through the extreme outward point;

identifying a middle point of the group of points; and
determining whether the middle point is inward relative to the outward boundary, the middle point being translated along a path generally perpendicular to the outward boundary to reside on the outward boundary where the middle point is inward relative to the outward boundary and the middle point being left in place where the middle point is on the outward boundary.

2. The method of claim 1, wherein the mating surface contours extend along at least one of an outer bone surface or an outer cartilage surface of the patient bone.

3. The method of claim 1, wherein the group of points includes three points.

4. The method of claim 1, wherein the inadequate segments include segments having at least one of: an imaging deficiency, a manufacturability constraint, or a surgical constraint.

5. The method of claim 1, wherein the inadequate segments include segments corresponding to portions of a mating surface of a customized arthroplasty jig configured such that the portions would not contact a corresponding surface of the patient bone when the mating surface of the customized arthroplasty jig matingly receives and contacts the surface of the patient bone.

6. The method of claim 1, wherein the patient bone is at least one of: a femur or a tibia.

7. The method of claim 1, further comprising:
outputting the smooth mating surface model to a machining system configured to produce a customized arthroplasty jig based on the smooth mating surface model.

8. One or more non-transitory tangible computer readable storage media storing computer-executable instructions for performing a computer process on a computing system, the computer process comprising:
segmenting sagittal slices of a volumetric image of a patient bone with segmentation splines;
generating an anatomically accurate model of the patient bone from the segmentation splines, the anatomically accurate model including anatomically accurate segmentation splines;
transforming the anatomically accurate segmentation splines into mating surface contours;
modifying any inadequate segments of the mating surface contours to obtain modified mating surface contours;
generating a mating surface model of the patient bone based on the mating surface contours and the modified mating surface contours; and
smoothing three-dimensional cross-sections of the mating surface model by removing one or more peaks and valleys in at least one curve of the three-dimensional cross-sections without encroaching into a region corresponding to inside the patient bone to generate a smooth mating surface model, wherein smoothing the three-dimensional cross-sections of the mating surface model comprises:
identifying a group of points extending along one of the mating surface contours, the group of points being part of points defining the mating surface contour;
identifying an extreme outward point of the points defining the mating surface contour;
defining an outer boundary extending through the extreme outward point;
identifying a middle point of the group of points; and
determining whether the middle point is inward relative to the outward boundary, the middle point being translated along a path generally perpendicular to the outward boundary to reside on the outward boundary where the middle point is inward relative to the outward boundary and the middle point being left in place where the middle point is on the outward boundary.

9. The one or more non-transitory tangible computer readable storage media of claim 8, wherein the mating surface contours extend along at least one of an outer bone surface or an outer cartilage surface of the patient bone.

10. The one or more non-transitory tangible computer readable storage media of claim 8, wherein the group of points includes three points.

11. A system comprising:
a computing device having at least one processor;
the computing device generating a smooth mating surface model having smoothed three-dimensional cross-sections of a mating surface model by removing one or more peaks and valleys in at least one curve of three-dimensional cross-sections without encroaching into a region corresponding to inside a patient bone, the mating surface model generated based on an anatomically accurate model of a patient bone, the anatomically accurate model generated from segmentation splines segmenting sagittal slices of a volumetric image of the patient bone;
the anatomically accurate model including anatomically accurate segmentation splines;
the at least one processor transforming the anatomically accurate segmentation splines into mating surface contours;
the at least one processor modifying any inadequate segments of the mating surface contours to obtain modified mating surface contours;
the at least one processor generating a mating surface model of the patient bone based on the mating surface contours and the modified mating surface contours; and
wherein the computing device smoothes the three-dimensional cross-sections of the mating surface model by:
identifying a group of points extending along one of the mating surface contours, the group of points being part of points defining the mating surface contour;
identifying an extreme outward point of the points defining the mating surface contour;
defining an outer boundary extending through the extreme outward point;
identifying a middle point of the group of points; and
determining whether the middle point is inward relative to the outward boundary, the middle point being translated along a path generally perpendicular to the outward boundary to reside on the outward boundary where the middle point is inward relative to the outward boundary and the middle point being left in place where the middle point is on the outward boundary.

12. The system of claim 11, further comprising:
a machining system producing the customized arthroplasty jig based on the smooth mating surface model.

13. The system of claim 11, wherein the patient bone is at least one of: a femur or a tibia.

* * * * *